US012571801B2

(12) United States Patent
Chang et al.

(10) Patent No.: US 12,571,801 B2
(45) Date of Patent: Mar. 10, 2026

(54) TANDEM ACTIVITY-BASED SENSING AND LABELING STRATEGY FOR REACTIVE OXYGEN SPECIES IMAGING

(71) Applicant: The Regents of the University of California, Oakland, CA (US)

(72) Inventors: Christopher J. Chang, Berkeley, CA (US); Hidefumi Iwashita, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 415 days.

(21) Appl. No.: 18/363,714

(22) Filed: Aug. 1, 2023

(65) Prior Publication Data

US 2023/0384315 A1 Nov. 30, 2023

Related U.S. Application Data

(63) Continuation of application No. PCT/US2022/013212, filed on Jan. 21, 2022.

(60) Provisional application No. 63/148,115, filed on Feb. 10, 2021.

(51) Int. Cl.

*G01N 33/58* (2006.01)
*C07F 5/02* (2006.01)

(52) U.S. Cl.

CPC .......... *G01N 33/582* (2013.01); *C07F 5/027* (2013.01)

(58) Field of Classification Search

None

See application file for complete search history.

(56) References Cited

U.S. PATENT DOCUMENTS 8,791,258 B2 * 7/2014 Chang .................... C07F 5/025 549/213

OTHER PUBLICATIONS

Grant & Hackh's Chemical Dictionary (5th Ed. 1987) at p. 148.*
International Search Report, Written Opinion, in priority application PCT/US22/13212, 6 pages (Apr. 12, 2022).
Iwashita et al. "A tandem activity-based sensing and labeling strategy enables imaging of transcellular hydrogen peroxido signaling", PNAS, Feb. 23, 2021. vol. 118 No. 9 e2018513118, 9 pages, entire document.

* cited by examiner

*Primary Examiner* — Po-Chih Chen

(74) *Attorney, Agent, or Firm* — Richard Aron Osman

(57) ABSTRACT

Selective probes provide tandem activity-based sensing and labeling of reactive oxygen species (ROS), such as hydrogen peroxide, peroxynitrite, and organic peroxides.

20 Claims, 9 Drawing Sheets

5
(PG1-FM)

6

TANDEM ACTIVITY-BASED SENSING AND LABELING STRATEGY FOR REACTIVE OXYGEN SPECIES IMAGING

This invention was made with government support under Grant Numbers ES028096 and GM139245 awarded by the National Institutes of Health. The government has certain rights in the invention.

INTRODUCTION

Reactive oxygen species (ROS) are a family of small molecules that play broad roles in physiology and pathology (1-6). In this context, hydrogen peroxide ($H_2O_2$) is a ROS that is both a source of oxidative stress and a potent signaling molecule. $H_2O_2$ has been shown to regulate cell growth, differentiation, migration, and death pathways. Indeed, beyond its classical roles in phagocytic killing of pathogens during immune response (7-9), production of $H_2O_2$ via superoxide by NADPH oxidase (Nox) enzymes in non-phagocytic cells (10) can trigger signaling events that contribute to a diverse array of physiological processes, including neural activity and long-term potentiation (11-14) and depression, stem cell growth and proliferation (15-17), circadian rhythms (18-20), and wound healing (21-22).

Owing to its transient and reactive nature, the vast majority of studies on $H_2O_2$ signaling have focused on intracellular communication events. Indeed, despite its small size and relatively non-polar nature, $H_2O_2$ is not freely diffusible through membranes and its entry into cells is tightly regulated, as our laboratory (23) and others (24-27) have identified specific isoforms of aquaporin water channels as endogenous mediators of $H_2O_2$ transport. As such, roles for $H_2O_2$ in transcellular communication remain insufficiently understood. This gap in fundamental knowledge is due in part to limitations in chemical tools to visualize integrated $H_2O_2$ activity that can retain spatial information over larger and/or more complex cell populations. Conventional small-molecule fluorescent probes for $H_2O_2$ can quickly access sites of local $H_2O_2$ elevations but can also diffuse away after ROS detection (28-40), diluting signal-to-noise responses. Likewise, traditional fluorescent protein-based indicators that reversibly respond to $H_2O_2$ can be localized by genetic encoding but are limited to studies within a microscope's field of view (41-45) and do not provide a permanent signal.

SUMMARY OF THE INVENTION

We disclose a tandem activity-based sensing and labeling strategy for reactive oxygen species imaging that enables capture and permanent recording of localized reactive oxygen species fluxes. As examples, Peroxy Green-1 Fluoromethyl (PG1-FM), Peroxy Red-1 Fluoromethyl (PR1-FM), and MitoPY1 Fluoromethyl (MitoPY1-FM) are representative diffusible small-molecule probes that sense the reactive oxygen species, hydrogen peroxide, by a boronate oxidation reaction to trigger dual release and covalent labeling of a fluorescent product, thus preserving spatial information on local reactive oxygen species changes. Such reagents enable visualizing of reactive oxygen species fluxes in whole cytosol with two different color probes and in mitochondria. Alternative suitable xanthene-based cores may also be derived from previously developed labels, e.g. Wang et al. Nature Chem 12, 165-72, February 2020. This work provides chemical probes that can achieve high spatial fidelity by combining activity-based sensing and labeling strategies.

The invention provides methods, compositions and systems comprising reactive oxygen species (ROS) sensors. In an aspect the invention provides a reactive oxygen species (ROS) sensor compound comprising a structure:

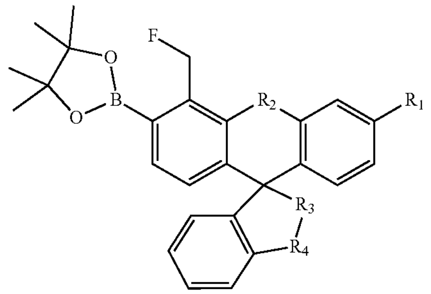

wherein:

R1 is OR5 or NR6R7, wherein R5, R6 and R7 are independently H, C1-C18 optionally substituted, optionally hetero-hydrocarbyl, or optionally substituted heteroatom, and R6/R7 are optionally joined to form a ring;

R2 is O, S, Se or Te, or an oxidized chalcogen like SO, $SO_2$, SS, SOS, SSS, SeO, $SeO_2$, SeS, SeOS, SeSS, TeO, $TeO_2$, TeS, TeOS, TeSS; or CR8R9, SiR8R9, GeR8R9, or PR8R9; or NR10, BR10, or PR10; wherein R8-R10 are independently H, C1-C18 optionally substituted, optionally hetero-hydrocarbyl, or optionally substituted heteroatom;

R3 is O, S, Se, Te, or NR11, wherein R11 is H, C1-C18 optionally substituted, optionally hetero-hydrocarbyl, or optionally substituted heteroatom; and R4 is C, Si, C═O, or C═NR12, wherein R12 is H, C1-C18 optionally substituted, optionally hetero-hydrocarbyl, or optionally substituted heteroatom; or a salt, hydrate or stereoisomer of the sensor.

In embodiments:

R1 is OR5 or NR6R7, wherein R5, R6 and R7 are independently H or C1-C18 optionally substituted, optionally hetero-alkyl, and R6/R7 are optionally joined to form a ring;

R2 is O, S, Se or Te, or an oxidized chalcogen like SO, $SO_2$, SS, SOS, SSS, SeO, $SeO_2$, SeS, SeOS, SeSS, TeO, $TeO_2$, TeS, TeOS, TeSS; or CR8R9, SiR8R9, GeR8R9, or PR8R9; or NR10, BR10, or PR10; wherein R8-R10 are independently H or C1-C18 optionally substituted, optionally hetero-alkyl;

R3 is O, S, Se, Te, or NR11, wherein R11 is H, C1-C18 optionally substituted, optionally hetero-alkyl;

R4 is C, Si, C═O, or C═NR12, wherein R12 is H, C1-C18 optionally substituted, optionally hetero-alkyl;

R1 is OMe or NR6R7, wherein R5 is Me, and R6 and R7 are independently C1-C4 optionally substituted, optionally hetero-alkyl, and R6/R7 are optionally joined to form a ring;

R2 is O or $Si(CH_3)_2$;

R3 is O;

R4 is C═O the compounds comprises a structure selected from:

14

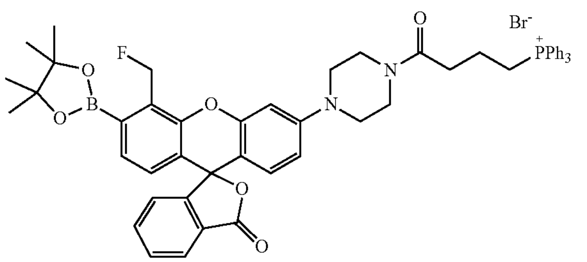

(MitoPY1-FM)

17

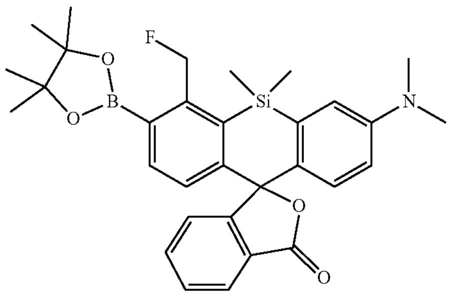

(PR1-FM)

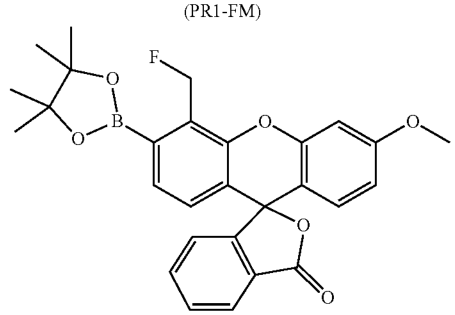

PG1-FM the compound is a bromide (Br) salt; and/or the ROS is selected from hydrogen peroxide ($H_2O_2$), peroxynitrite, and organic peroxides (e.g. lipid peroxides, explosive peroxides);

the compound provides boronate oxidation sensing and/or quinone methide labeling sequence upon reaction with the ROS; and/or the compounds provides tandem boronate oxidation sensing and quinone methide labeling sequence upon reaction with the ROS, preferably to covalently trap the probe in a cell and afford a stain that preserves spatial information on localized ROS fluxes.

In an aspect the invention provides a method of using the subject compounds comprising: selectively detecting the ROS with the compound.

The invention encompasses all combinations of the particular embodiments recited herein, as if each combination had been laboriously recited, such as wherein

DESCRIPTION OF PARTICULAR EMBODIMENTS OF THE INVENTION

Figure 1A:
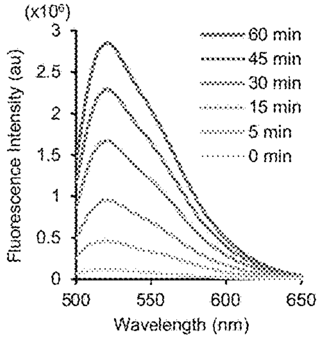
FIGS. 1A-I. Fluorescence responses and activity-based sensing and labeling properties of PG1-FM, MitoPY1-FM, and PR1-FM. (A, B, C) Activity-based sensing fluorescence responses of 1 μM PG1-FM (A), 1 μM MitoPY1-FM (B), and 1 μM PR1-FM (C) to 25 μM $H_2O_2$. Data were acquired in PBS (pH 7.4) at 37° C. (D, E, F) Fluorescence responses of 1 μM PG1-FM (D), 1 μM MitoPY1-FM (E), and 1 μM PR1-FM (F) towards biologically relevant competing reactive oxygen species and reactive nitrogen species. (G, H, I) $H_2O_2$-dependent activity-based labeling of PG1-FM (G), MitoPY1-FM (H), and PR1-FM (I) to BSA. A solution of BSA (0.5 mg/mL) and PG1-FM (1 μM), MitoPY1-FM (1 μM), and PR1-FM (1 μM) in PBS (pH 7.4) was incubated with or without $H_2O_2$(100 μM) and analyzed by SDS-PAGE gel.

Unless contraindicated or noted otherwise, in these descriptions and throughout this specification, the terms "a" and "an" mean one or more, the term "or" means and/or. The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicylclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R"', —OC(O)R', —C(O)R', —CO2R', —CONR'R"', —OC(O)NR'R', —NR"C(O)R', —NR'—C(O)NR"R"', —NR'—SO2NR"', —NR"CO2R', —NH—C (NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds/sensors/probes of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurommethyl ether (OCF3).

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl $—CH_2C(O)—$ groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

The compounds may in the form of salts, such as hydrochlorides, hydrobromides, acetates, sulfates, citrates, carbonates, trifluoroacetates and the like. Suitable salts include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with $HOOC—(CH_2)n-COOH$, wherein n is selected from 0 to 4. Examples of suitable cations include, but are not limited to, sodium, potassium, calcium, aluminum, lithium, and ammonium. Examples of base addition salts include sodium, potassium, calcium, ammonium, organic amino, or magnesium salts, or the like. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

In addition, if a compound is obtained as an acid addition salt, the free base can be obtained by basifying a solution of the acid salt. Conversely, if the product is a free base, an addition salt, such as an addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare addition salts, particularly non-toxic salts.

The term “at least one substituent” includes, for example, from 1 to 4, such as from 1 to 3, further as 1 or 2, substituents. For example, “at least one substituent $R^{16}$” herein includes from 1 to 4, such as from 1 to 3, further as 1 or 2, substituents selected from the list of $R^{16}$ as described herein.

Certain compounds can exist in unsolvated forms as well as solvated forms, including hydrated forms. In general, the solvated forms are equivalent to unsolvated forms, and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

EXAMPLES

A Tandem Activity-Based Sensing and Labeling Strategy Enables Imaging of Transcellular Hydrogen Peroxide Signaling In this example we report a dual activity-based sensing and labeling strategy for selective and sensitive fluorescence detection of $H_2O_2$ with the ability to capture and record spatial information over defined time scales. Peroxy Green-1 Fluoromethyl (PG1-FM, Scheme 1) promotes a tandem boronate oxidation sensing and quinone methide labeling sequence upon reaction with $H_2O_2$ to covalently trap the probe in cells and afford a permanent stain that preserves spatial information on localized $H_2O_2$ fluxes. PG1-FM is capable of monitoring elevations in endogenous $H_2O_2$ production in live cells and is useful for both microscopy and flow cytometry assays. As an example of its utility, we use this probe to visualize of transcellular ROS signaling in a microglia-neuron co-culture system. This approach provides a combined chemical sensing and labeling strategy to decipher biology with improved spatial fidelity.

Designs of Peroxy Green-1 Fluoromethyl (PG1-FM) and MitoPY1 Fluoromethyl (MitoPY1-FM), and Peroxy Red 1 Fluoromethyl (PR1-FM).

The designs of PG1-FM and MitoPY1-FM combines the reliable boronate trigger established by our laboratory for activity-based sensing of $H_2O_2$ (28, 31, 33) with a pendant fluoromethyl group ortho to this cage that serves as a latent quinone methide species for proximal covalent labeling upon $H_2O_2$-mediated boronate-to-phenol conversion (Scheme 1 and Scheme 2). This tandem sensing/labeling strategy affords the ability to trap the probe at the site of $H_2O_2$ reactivity. We were inspired by elegant studies by Urano and colleagues on the use of fluoromethyl arenes as latent electrophiles for cell-specific labeling and killing purposes (46-48) with single-cell resolution. In the absence of $H_2O_2$, the fluoromethyl aryl boronate probe is freely diffusible throughout the cell and between cells as it is membrane-permeable. However, upon reaction with $H_2O_2$, conversion of the boronate to the corresponding phenol triggers fluoride elimination to generate a highly reactive quinone methide electrophile, which when generated intracellularly, can be locally captured by proximal protein-based nucleophiles, leaving a fluorescent product covalently labeled at the site of the activity-based sensing reaction. A key advance enabled by the design feature of this approach compared to conventional small-molecule fluorophores is that it minimizes background signal from extracellular $H_2O_2$ reactivity and entry of the oxidized probe into cells, in contrast to previous probes that rely on esterase trapping and give signal from dyes both before and after reaction with $H_2O_2$ (15, 23). Indeed, in this tandem sensing and labeling strategy, oxidized dye products would be largely quenched by either water or extracellular protein nucleophiles and rendered membrane-impermeable, where they can be readily washed away from the cell. This feature results in enhanced signal-to-noise responses from localized intracellular $H_2O_2$ fluxes. As such, this tandem activity-based sensing and labeling strategy uniquely enables visualization of $H_2O_2$ with the ability to retain and record permanent spatial information in both live- and fixed cell settings by covalent modification. Moreover, this dual activity-based sensing/labeling approach is generally applicable to the design of a broader array of probes for other biological analytes of interest. Furthermore, to apply this tandem sensing/labeling strategy to in vivo imaging, we also synthesized PR1-FM which is a silicon rhodol-based fluorophore and achieved $H_2O_2$ visualization with Zebrafish (Scheme 3).

PG1-FM, MitoPY1-FM, and PR1-FM are a Dual Activity-Based Sensing and Labeling Probe with Hydrogen Peroxide and Protein Substrates.

Figure 9A:
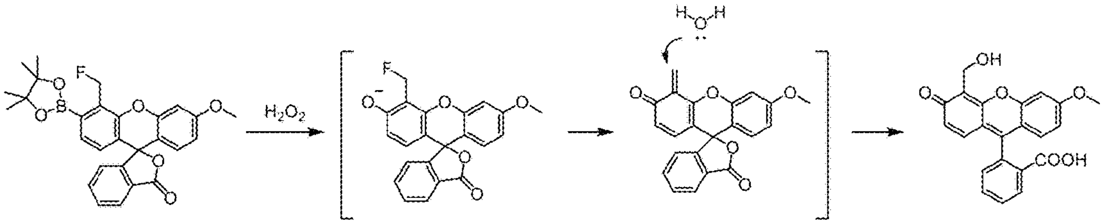
FIGS. 9A-B. The reaction mechanism (A) and HPLC analyses (B) of the reaction product using PG1-FM and $H_2O_2$. 10 μM PG1-FM was treated with 10 μM $H_2O_2$ in PBS (−), containing 1% DMSO, and the mixture was incubated at 37° C. for 30 min. HPLC analysis was performed under a gradient condition (A: $H_2O$ containing 0.05% formic acid; B: acetonitrile containing 0.05% formic acid; A/B=75%/25% to 25%/75% in 15 min). Absorbance at 254 nm and 470 nm were monitored. The spectra show before (blue) and after (orange) reaction with $H_2O_2$, and its putative product, hydroxymethyl compound 6 (green), which is obtained by boronate deprotection and quenching of the quinone methide by water.
Figure 9B:
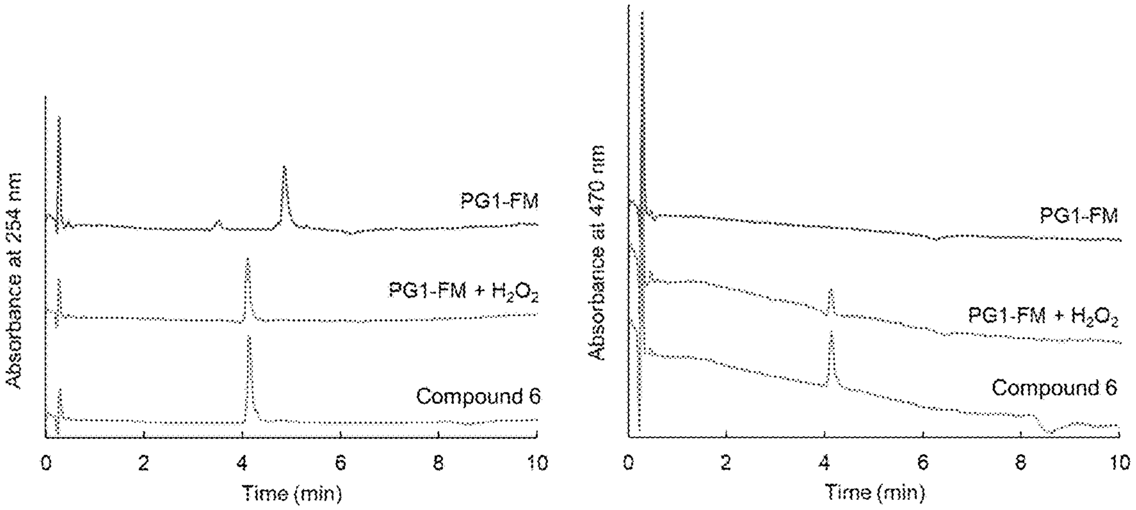
Figure 10:
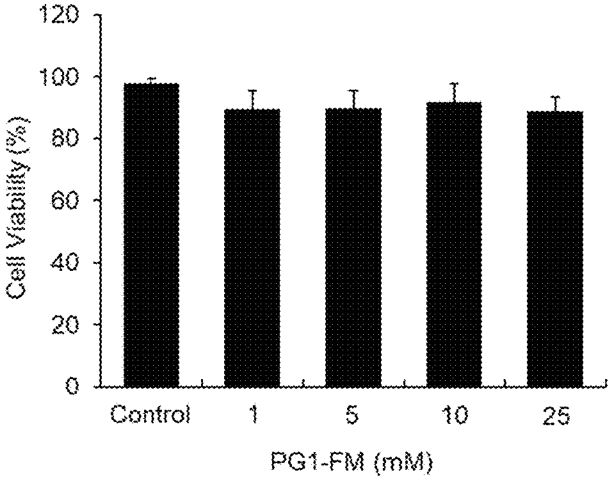
FIG. 10. Cell viability assay of PG1-FM to HeLa cells. The cells were incubated with PG1-FM (1, 5, 10, and 25 μM) for 1 h at 37° C. under 5% $CO_2$ incubator. The medium was replaced with fresh medium containing Cell Counting Kit-8 (Dojindo Laboratories, Japan), then measured with a microplate reader at 450 nm absorption after incubating for 2 h. Data represent mean and a.d. (n=6).

We first evaluated the in vitro response of PG1-FM, MitoPY1-FM, and PR1-FM to hydrogen peroxide in aqueous solution buffered to physiological pH. As expected by their activity-based sensing boronate trigger, the probes exhibited a clear fluorescence enhancement after treatment with $H_2O_2$(FIG. 1A-C). PG1-FM converted to a fluorescent product that undergoes subsequent hydrolysis with $H_2O$ by LC analysis (FIG. 9A-B). Moreover, PG1-FM, MitoPY1-

Figure 1D:
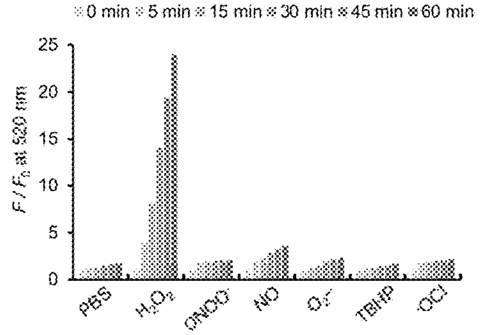
Figure 1G:
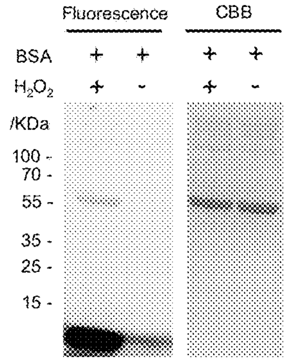
Figure 1B:
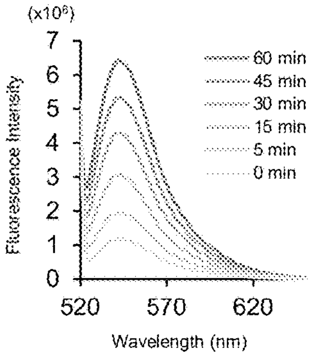
Figure 1E:
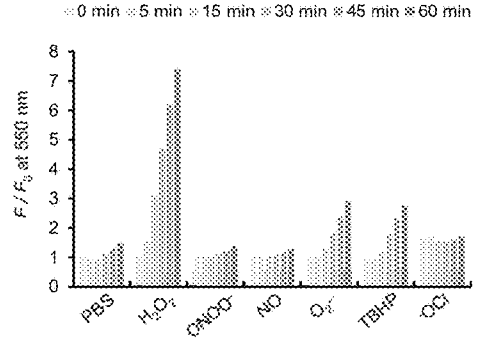
Figure 1H:
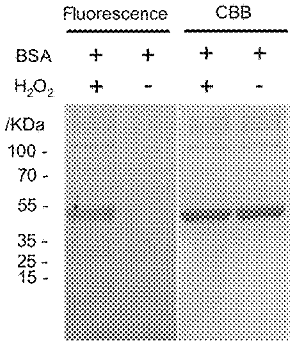
Figure 1C:
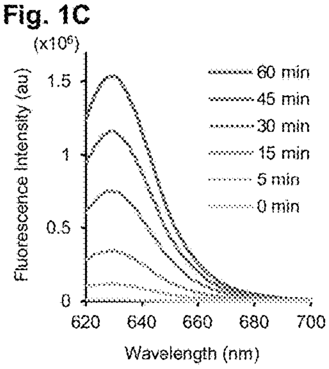
Figure 1F:
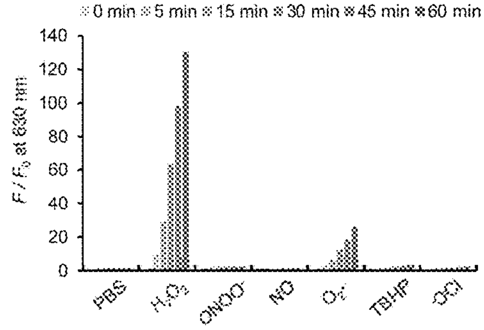
Figure 1I:
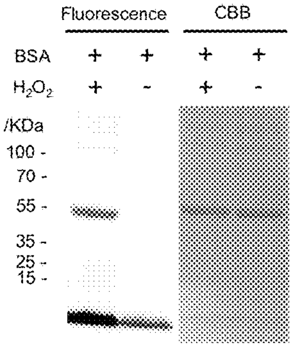

FM, and PR1-FM gave a highly selective response for $H_2O_2$ over other biologically relevant reactive oxygen species and reactive nitrogen species congeners (FIG. 1D-F). To establish activity-based labeling of PG1-FM, MitoPY1-FM, and PR1-FM in a $H_2O_2$-dependent manner, we incubated the probes with bovine serum albumin (BSA) as a model protein substrate in the presence or absence of $H_2O_2$, and the reactions were analyzed by SDS-PAGE. A fluorescent BSA-associated band was observed only under conditions with $H_2O_2$, consistent with $H_2O_2$-dependent labeling of the protein with the dye (FIG. 1G-I) (28, 30). These data establish that PG1-FM, MitoPY1-FM, and PR1-FM are $H_2O_2$-responsive and $H_2O_2$-selective fluorescent probes that can undergo a secondary labeling reaction with a model protein upon activity-based sensing.

PG1-FM, MitoPY1-FM, and PR1-FM Can Monitor Elevations in $H_2O_2$ Levels in Live Cells with Exogenous Peroxide Treatment.

Figure 2A:
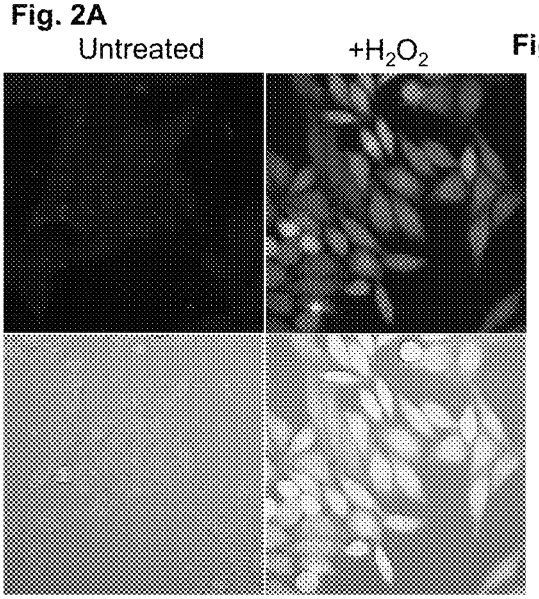
FIGS. 2A-C. Exogenous $H_2O_2$ detection. Confocal microscopic images of HeLa cell stained with PG1-FM, PR1-FM, and MitoPY1-FM. (A, B) HeLa cells were pe-stained with PG1-FM (5 μM) or PR1-FM (5 μM) at 37° C. in a 5% $CO_2$ incubator. After incubating for 30 min, the cells were washed with HBSS twice, and treated with $H_2O_2$ (1 mM) for 60 min. The cells were observed on confocal microscope after washing with HBSS twice. (C) HeLa cells were pe-stained with MitoPY1-FM (5 μM) at 37° C. in a 5% $CO_2$ incubator. After incubating for 30 min, the cells were washed with HBSS twice, and treated with $H_2O_2$ (1 mM) for 60 min. The cells were observed on confocal microscope after staining with MitoBright LT Green for 30 mi. Scale bar: 50 μm.
Figure 2B:
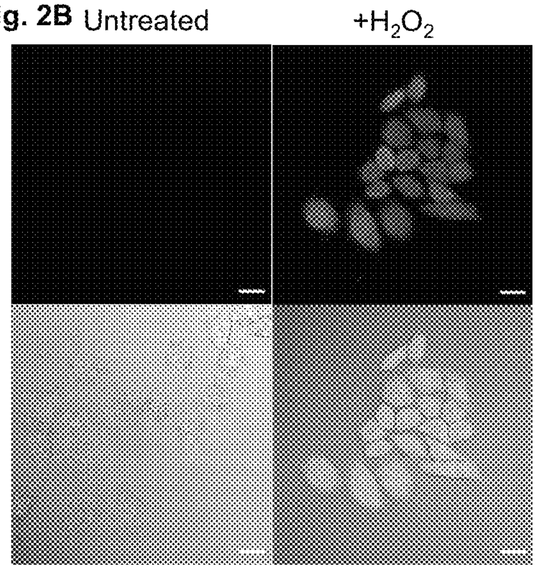
Figure 2C:
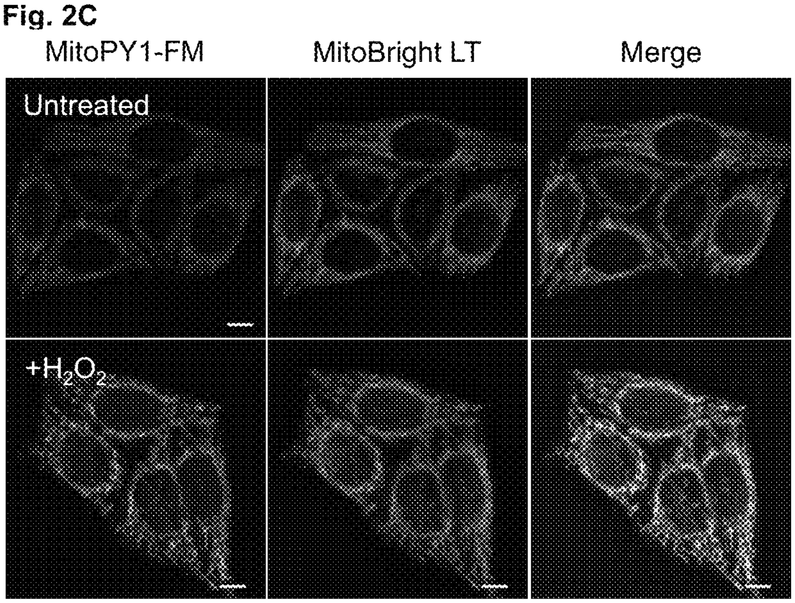

We next assessed the ability of PG1-FM, MitoPY1-FM, and PR1-FM for visualizing changes in $H_2O_2$ levels in live cells with exogenous $H_2O_2$ treatment. HeLa cells were pre-stained with 5 μM of PG1-FM, MitoPY1-FM, or PR1-FM, treated with $H_2O_2$ (1 mM) or vehicle control, washed, and imaged. MitoPY1-FM stained HeLa cells were co-stained with MitoBright LT Green before imaging. PG1-FM and PR1-FM showed fluorescence increase in the whole cells (FIGS. 2A and 2B). MitoPY1-FM was overlapped with MitoBright LT (FIG. 2C). We observed that the probes load evenly throughout the cell and responds to elevations in $H_2O_2$(FIGS. 2A, 2B, and 2C). Moreover, these data show that the dual activity-based sensing/labeling strategy is viable for live-cell $H_2O_2$ imaging.

PG1-FM and PR1-FM Can Image Endogenous $H_2O_2$ Production in Live Cells during oxidative stress or redox signaling.

Figure 3A:
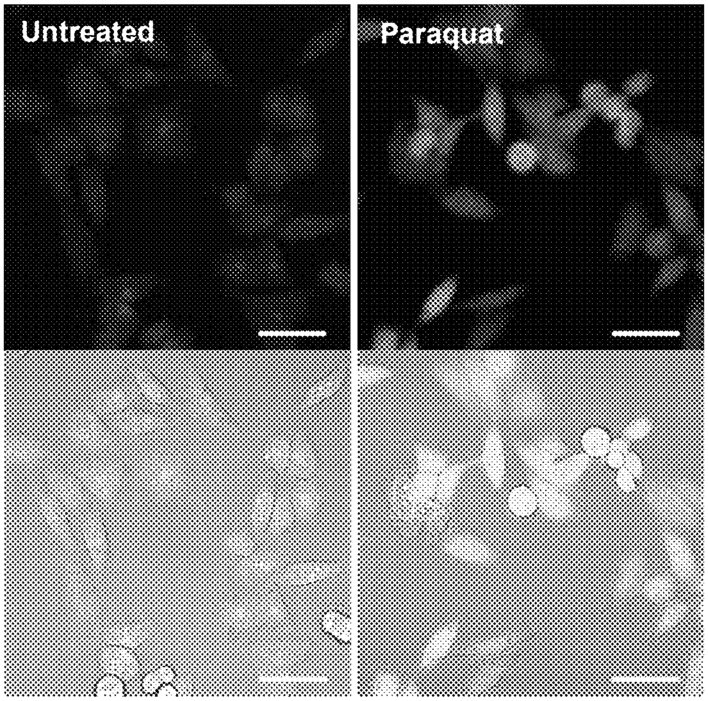
FIGS. 3A-C. PG1-FM imaging of endogenous $H_2O_2$ generation in live HeLa cells under oxidative stress conditions stimulated by paraquat. (A) Confocal microscopy images of HeLa cells treated with or without paraquat (1 mg/mL) for 24 h, stained with PG1-FM (10 μM) for 1 h, washed twice with HBSS, and imaged. Scale bar: 50 μm. (B) Flow cytometry analysis of the cells treated with or without paraquat using PG1-FM using same conditions as (A). (C) Flow cytometric data quantified with mean value. **P<0.01.
Figure 3B:
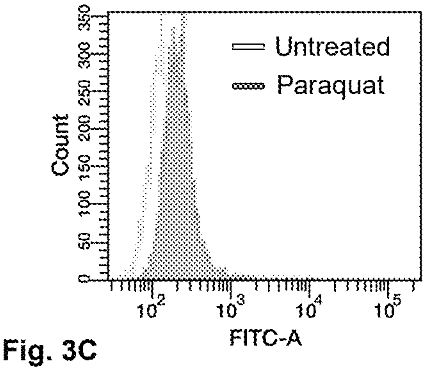
Figure 3C:
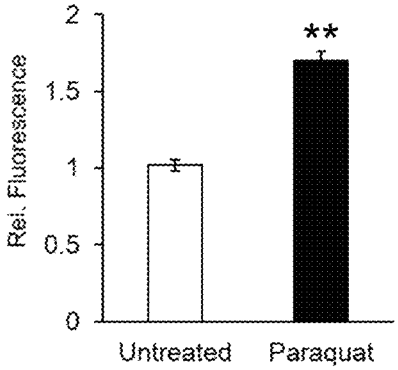

We next utilized PG1-FM for imaging endogenous $H_2O_2$ fluxes produced by multiple types of cell models under various stimulation conditions. Our first set of experiments along these lines evaluated the performance of the probe under conditions of oxidative stress induced by paraquat treatment. HeLa cells were stimulated with or without paraquat (1 mg/mL) for 24 h to induce ROS and oxidative stress, followed by staining with PG1-FM for 30 min, washing, and imaging. HeLa cells exposed to paraquat showed patent $H_2O_2$-dependent fluorescence increases compared to untreated counterparts as observed by confocal microscopy (FIG. 3A). Because the probe is cell-trappable, we verified the observed fluorescence enhancements using flow cytometry (FIG. 3B, 3C), highlighting its utility in this analytical method as well.

Figure 4A:
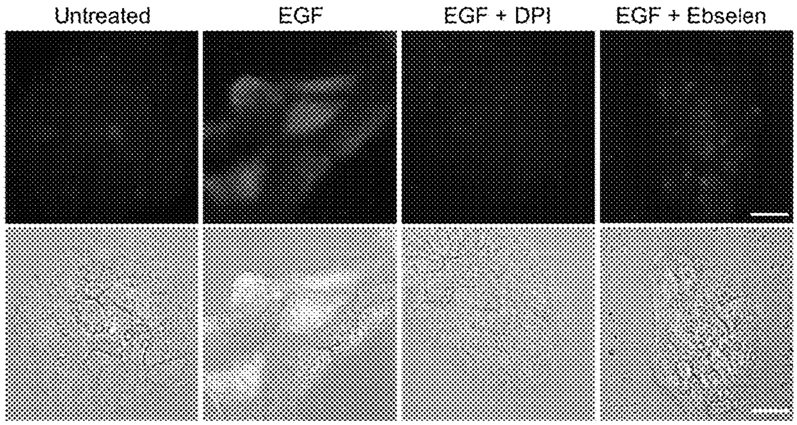
FIGS. 4A-B. PG1-FM imaging of endogenous $H_2O_2$ generation in live A431 cells under redox signaling conditions with epidermal growth factor (EGF) stimulation. (A) Confocal microscopy (top row) and overlaid brightfield (bottom row) images of A431 cells stained with PG1-FM (10 μM) and then treated with EGF (1 μg/mL) or vehicle control for 30 min, washed and imaged, or first pre-treated with NADPH oxidase inhibitor DPI (5 μM) or antioxidant ebselen (5 μM) for 30 min in HBSS solution before PG1-FM staining and EGF stimulation. (B) Quantification of experiments. Scale bar: 20 μm. *P<0.05.
Figure 4B:
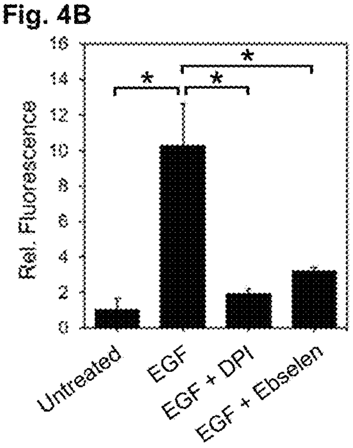
Figure 5A:
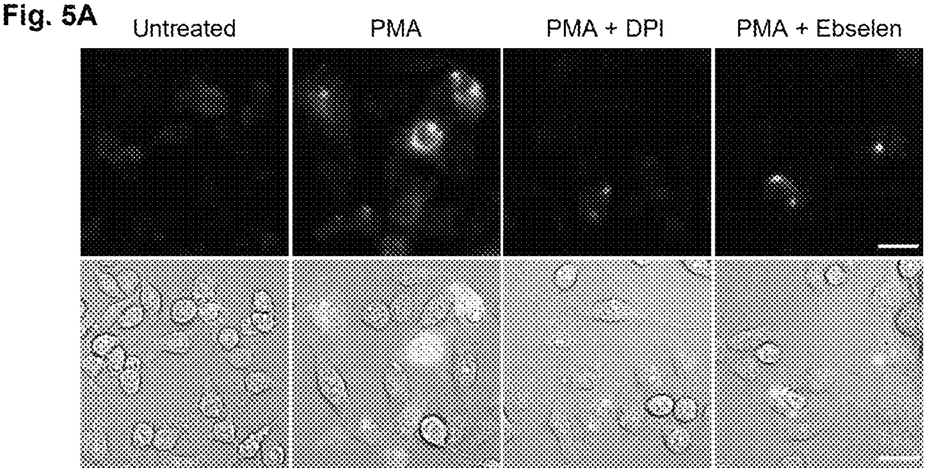
FIGS. 5A-D. PG1-FM and PR1-FM imaging of endogenous $H_2O_2$ generation in live RAW264.7 macrophage cells under inflammatory immune response conditions with phorbol 12-myristate 13-acetate (PMA) stimulation. (A) Confocal microscopy (top row) and overlaid brightfield (bottom row) images of RAW264.7 macrophages stained with PG1-FM (10 μM) and then treated with PMA (1 μg/mL) or vehicle control for 60 min, washed and imaged, or first pre-treated with NADPH oxidase inhibitor DPI (5 μM) or antioxidant ebselen (5 μM) for 30 min in HBSS solution before PG1-FM staining and PMA stimulation. (B) Flow cytometry histograms and (C) quantification of mean value fluorescence intensity using PG1-FM under same conditions as (A). (D) Confocal microscopic images of RAW264.7 macrophages stained with PR1-FM (10 μM) under same conditions as (A). **P<0.01. Scale bar: 20 μm.
Figure 5B:
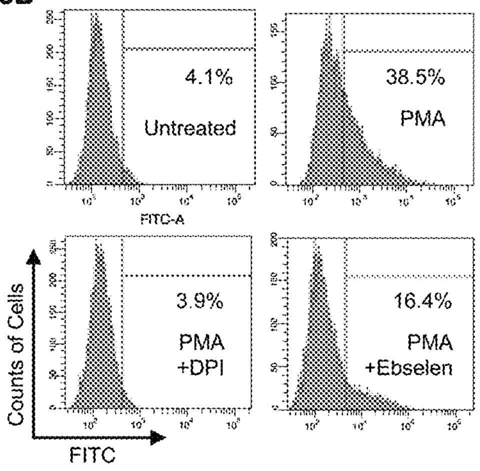
Figure 5C:
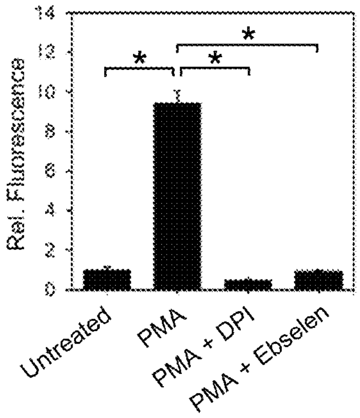
Figure 5D:
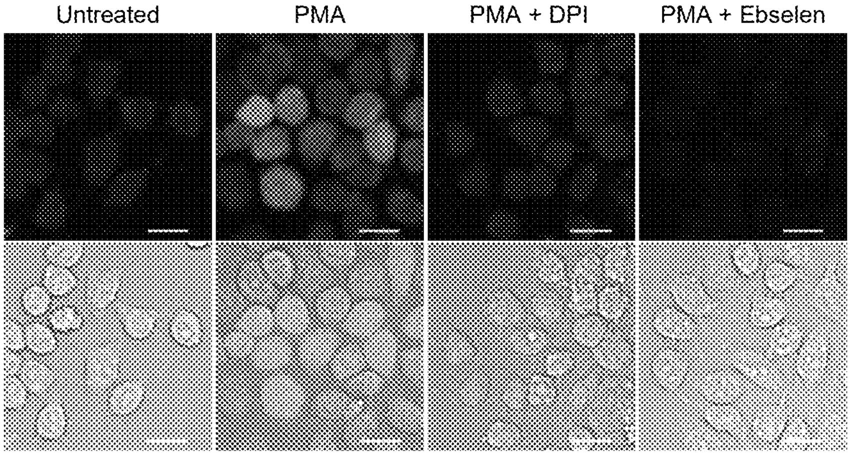

We next applied PG1-FM to detect endogenous $H_2O_2$ produced by growth factor stimulation in A431 cells, a skin cancer cell line that has high expression levels of the epidermal growth factor receptor (EGFR) and is known to generate $H_2O_2$ by stimulation with EGF through NADPH oxidase (Nox) activity (32, 50). Owing to the fast generation of $H_2O_2$ by EGF stimulation relative to paraquat, A431 cells were stained with PG1-FM first and then treated with 1 μg/mL of EGF or vehicle control for 30 min, washed, and imaged. Confocal microscopy images show a clear increase in fluorescence for EGF-stimulated A431 cells over control counterparts (FIG. 4A). Moreover, addition of diphenyleneiodonium (DPI) as a broad-spectrum Nox inhibitor or ebselen as a general antioxidant quencher of $H_2O_2$ inhibited $H_2O_2$-induced enhancements in PG1-FM fluorescence (FIG. 4B).

We next tested the ability of PG1-FM and PR1-FM to monitor $H_2O_2$ production in RAW 264.7 macrophages. This mouse leukemia macrophage cell model is known to generate $H_2O_2$ via superoxide by stimulation with phorbol 12-myristate 13-acetate (PMA), which activates Nox through a protein kinase C (PKC)—dependent pathway (50). PMA (1 μg/mL)—treated cells for 60 min showed higher PG1-FM and PR1-FM fluorescence relative to control cells by both confocal microscopy and flow cytometry assays (FIG. 5A-D). Moreover, as observed for the EGF-stimulated A431 models, fluorescence increases are blocked by DPI or ebselen. Taken together, the collective results establish that the dual activity-based sensing/labeling probe PG1-FM is effective for detecting exogenous and endogenous changes in $H_2O_2$ levels across a range of cell models and stimulation conditions by both microscopy and flow cytometry.

In vivo Live Imaging of Endogenous Hydrogen Peroxide Production with Zebrafish

Figure 6:
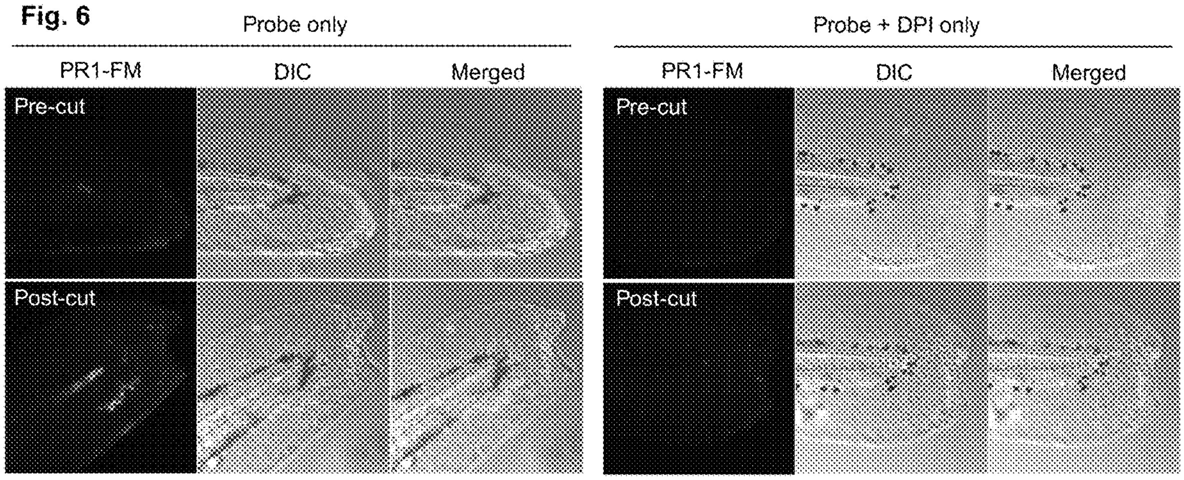
FIG. 6. Confocal microscopic images of zebrafish labeled with PR1-FM. Zebrafish embryos in E3 medium containing P1-FM (5 μM) were incubated overnight. The fishes were additionally incubated for 1 hour with containing DPI (100 nM) before the tail fin cut.

We sought to apply PR1-FM for in vivo live imaging to detect endogenous hydrogen peroxide production. PR1-FM was tested with live zebrafish in the regenerated fin model. The larvae at two days post-fertilization (dpf) was pre-stained with PR1-FM (5 μM) overnight before tail fin cut. Interestingly, PR1-FM exhibited patently higher fluorescence signals in post-cut condition compared to in pre-cut (FIG. 6). Moreover, addition of DPI as an inhibitor showed lower level of fluorescence under the same conditions (FIG. 6). These results indicated that hydrogen peroxide level around injury area increased upon cutting fin that might be induced oxidative stress. Taken together, PR1-FM can be useful for detecting hydrogen peroxide in live zebrafish.

MitoPY1-FM can Image Endogenous $H_2O_2$ Production in Live Cells During Oxidative Stress or Redox Signaling.

Figure 7A:
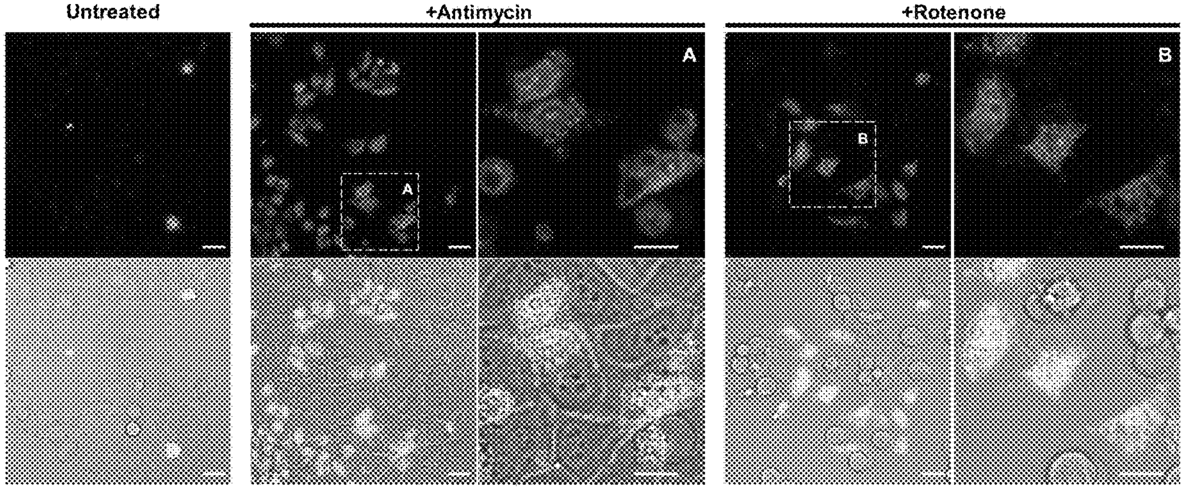
FIGS. 7A-B. Confocal microscopic images of HeLa cell stained with MitoPY1-FM. (A) HeLa cell was stained with MitoPY1-FM (5 μM) for 1 h. After washing the cell with non-FBS medium, the cell was treated with Antimycin (1 μM) or Rotenone (1 μM) for 24 h. The cells were observed on confocal microscope after washing the cell. (B) Confocal microscopic images of fixed HeLa cell stained with MitoPY1-FM and Tom 20 antibody. HeLa cells were stained with MitoPY1-FM and then exposed with antimycin A. The treated cells were fixed and stained with Tom 20 antibody before the observation.
Figure 7B:
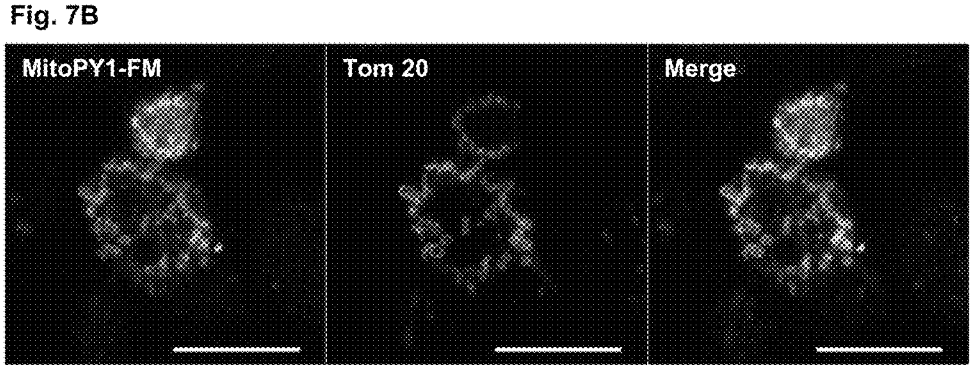
Figure 8:
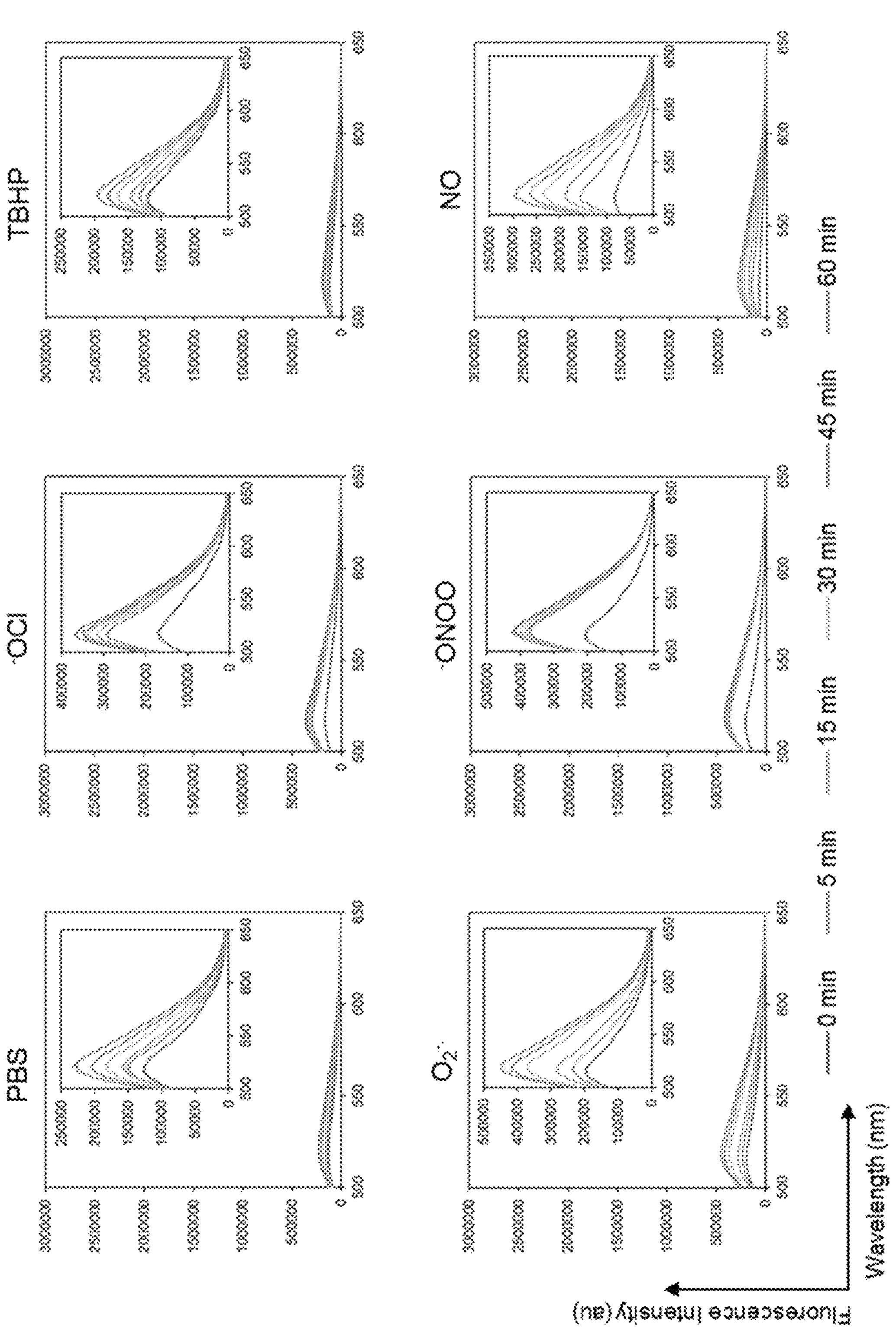
FIG. 8. Fluorescence spectra of PG1-FM reacted with 25 mM of $OCl^-$, TBHP, $O_2^-$, $ONOO^-$, NO or PBS (control). PG1-FM (1 μM) was incubated with 25 mM of $H_2O_2$, $OCl^-$, TBHP, $O_2^-$, $ONOO^-$, or NO at 37° C. in PBS (−). The mixtures were measured by fluorometer at any incubating times (0, 5, 15, 30, 45, and 60 min).

We evaluated MitoPY1-FM for imaging mitochondrial $H_2O_2$ fluxes produced by inhibition of mitochondrial electron transporter chain. HeLa cells were pre-stained with MitoPY1-FM (5 μM) and stimulated by Antimycin (1 μM) or Rotenone (1 μM) for 24 h to induce ROS and oxidative stress. Mitochondria exposed to inhibitors showed patent $H_2O_2$-dependent fluorescence increases compared to untreated counterparts as observed by confocal microscopy (FIG. 7A). Owing to the binding to the proteins, MitoPY1-FM was simultaneously use with Tom20 antibody and verified that the observed fluorescence of MitoPY1-FM enhanced on mitochondria (FIG. 7B).

We have presented the design, synthesis, and biological applications of a tandem activity-based sensing and labeling probe strategy for fluorescence imaging of $H_2O_2$ that enables the ability to provide an integrated recording of $H_2O_2$ fluxes with permanent retention of spatial resolution. PG1-FM, MitoPY1-FM, and PR1-FM feature an activity-based boronate trigger for selective and sensitive $H_2O_2$ detection coupled to a fluoromethyl moiety that serves as a latent quinone methide source for proximal covalent trapping upon the $H_2O_2$-mediated conversion of a boronate to phenol on the reporter probe. These unique reagents are capable of monitoring changes in $H_2O_2$ levels through endogenous sources across a range of cell types and stimulations using both microscopy and flow cytometry, including the direct observation of transcellular redox signaling between microglia and neurons in a co-culture model system where selective stimulation of microglia results in rises in intracellular levels of $H_2O_2$ in neighboring neurons. Microglial ROS production contributes to neuronal injury in neurodegenerative disorders, ischemic stroke, brain trauma, and other settings (51-55), but the transient nature of ROS in living cells has limited efforts to identify temporal and spatial aspects of these processes. Our invention provides tools to explore consequences of microglial and other sources of ROS diseasing these and related disorders. By directly visualizing $H_2O_2$ elevations triggered by transcellular activation, this work reveals a role for $H_2O_2$ and other ROS, in cell-to-cell communication more broadly.

On the chemistry side, owing to the variety of available phenol-based fluorophores, the fluoromethyl motif can serve as a latent masked quinone methide to produce probes spanning a palette of colors and additional targeting groups to further increase spatial and temporal resolution. Indeed, beyond applications for PG1-FM, PR1-FM, and MitoPY1-FM and related imaging probes for recording localized and integrated $H_2O_2$ activity in larger and more complex cell populations, the combination of activity-based sensing and labeling strategies can be applied to a broader range of analytes to decipher new biology (56-57).

REFERENCES

1. B. D' Autreaux, M. B. Toledano, ROS as Signaling molecules: mechanisms that generate specificity in ROS homeostasis, *Nat. Rev. Mol. Cell Biol.* 8, 813-824 (2007).
2. C. C. Winterbourn, Reconciling the chemistry and biology of reactive oxygen species, *Nature Chem. Biol.* 4, 278-286 (2008).
3. H. M. Cocheme' et al., Measurement of $H_2O_2$ within living drosophila during aging using a ratiometric mass spectrometry probe targeted to the mitochondrial matrix, *Cell Metabolism* 3, 340-350 (2011).
4. M. Schieber, N. S. Chandel, ROS Function in redox signaling and oxidative stress, *Curr. Biol.* 10, R453-R462 (2014).
5. D. Reichmann, W. Voth, U. Jakob, Maintaining a healthy proteome during oxidative stress, *Mol. Cell,* 69, 203-213 (2018).
6. H. Sies, D. P. Jones, Reactive oxygen species (ROS) as pleiotropic physiological signalling agents, *Nat. Rev. Mol. Cell Biol.* 21, 363-383 (2020).
7. M. C. Dinauer, S. H. Orkin, R. Brown, A. J. Jesaitis, C. A. Parkos, The glycoprotein encoded by the X-linked chronic granulomatous disease locus is a component of the neutrophil cytochrome b complex. *Nature* 327, 717-720 (1987).
8. B D. Volpp, W M Nauseef, R A. Clack, Two cytosolic neutrophil oxidase components absent in autosomal chronic granulomatous disease. *Science* 242, 295-1296 (1988).
9. R. A. Clark et al., Genetic variants of chronic granulomatous disease: prevalence of deficiencies of two cytosolic components of the NADPH oxidase system. *N. Engl. J. Med.* 321, 647-652 (1989).
10. J. D. Lambeth, NOX enzyme and the biology of reactive oxygen. *Nature Rev. Immunol.* 4, 181-189 (2004).
11. A. Kamsler, M. Segal, Hydrogen peroxide modulation of synaptic plasticity. *J. Neurosci.* 23, 269-276 (2003).
12. M. V. Tejada-Simon et al., Synaptic localization of a functional NADPH oxidase in the mouse hippocampus. *Mol. Cell Neurosci.* 29, 97-106 (2005).
13. A. M. Brennan, NADPH oxidase is the primary source of superoxide induced by NMDA receptor activation. *Nature Neurosci.* 12, 857-863 (2009).
14. R. D. Pasquale et al., LTP and LTD in the visual cortex require the activation of NOX2. *J. Neurosci.* 34, 12778-12787 (2014).
15. B. C. Dickinson et al., Nox2 redox signaling maintains essential cell populations in the brain. *Nature Chem. Biol.* 7, 106-112 (2011).
16. J. Le Belle et al., Proliferative neural stem cells have high endogenous ROS levels that regulate self-renewal and neurogenesis in a PI3K/Akt-dependant manner. *Cell Stem Cell,* 8, 59-71 (2011).
17. C. Xu, et al, Oxidative stress induces stem cell proliferation via TRPA1/RyR-mediated $Ca^{2+}$ signaling in the Drosophila midgut. *eLife,* 6, e22441 (2017).
18. C. S. O'Neill, A. B. Reddy, Circadian clocks in human red blood cells. *Nature,* 469 498-503 (2011).
19. R. S. Wible et al., NRF2 regulates core and stabilizing circadian clock loops, coupling redox and timekeeping in Mus musculus. *eLife,* 7, e31656 (2018).
20. J. F. Pei et al., Diurnal oscillations of endogenous $H_2O_2$ sustained by $p^{66shc}$ regulate circadian clocks. *Nature Cell Biol.,* 21, 1553-1564 (2019).
21. P. Niethammer, C. Grabher, A. T. Look, T. J. Mitchison, A tissue-scale gradient of hydrogen peroxide mediates rapid wound detection in zebrafish. *Nature* 459, 996-999 (2009).
22. A. Hervera et al., Reactive oxygen species regulate axonal regeneration through the release of exosomal NADPH oxidase 2 complexes into injured axons. *Nature Cell Biol.* 20, 307-319 (2018).
23. E. W. Miller, et al, Aquaporin-3 mediates hydrogen peroxide uptake to regulate downstream intracellular signaling. *Proc. Natl. Acad. Sci. U.S.A.* 107, 15681-15686 (2010).
24. G. P. Beinert et al., Specific aquaporins facilitate the diffusion of hydrogen peroxide across membranes. *J. Biol. Chem.* 282, 1183-1192 (2007).
25. M. Dynowski, G. Schaaf, D. Loque, O. Moran, U. Ludewig, Plant plasma membrane water channels conduct the signalling molecule $H_2O_2$, *Biochem. J.* 414, 53-61 (2008).
26. O. Rodrigues, et al. Aquaporins facilitate hydrogen peroxide entry into guard cells to mediate ABA- and pathogen-triggered stomatal closure. *Proc. Natl. Acad. Sci. U.S.A.* 114, 9200-9205 (2017).
27. C. Rodrigues et al., Human aquaporin-5 facilitates hydrogen peroxide permeation affecting adaption to oxidative stress and cancer cell migration. *Cancers* 11, 932 (2019).
28. A. R. Lippert, et al, Boronate oxidation as a bioorthogonal reaction approach for studying the chemistry of hydrogen peroxide in living systems. *Acc. Chem. Res.* 44, 793-804 (2011).
29. T. F. Brewer, F. J. Garcia, C. S. Onak, K. S. Carroll, C. J. Chang, Chemical approaches to discovery and study of sources and targets of hydrogen peroxide redox signaling through NADPH oxidase proteins. *Annu. Rev. Biochem.* 84, 765-790 (2015).
30. M. C. Y. Chang, A. Pralle, E. Y. Isacoff, C. J. Chang, A selective, cell-permeable optical probe for hydrogen peroxide in living cells. *J. Am. Chem. Soc.* 126, 15392-15393 (2004).
31. H. Maeda, et al. Fluorescent probes for hydrogen peroxide based on a non-oxidative mechanism, *Angew. Chem. Int. Ed.* 43, 2389-2391 (2004).
32. E. W. Miller, O. Tulyathan, E. Y. Isacoff, C. J. Chang, Molecular imaging of hydrogen peroxide produced for cell signaling. *Nature Chem. Biol.* 3, 263-267 (2007).
33. B. C. Dickinson, C. J. Chang, A targetable fluorescent probe for imaging hydrogen peroxide in the mitochondria of living cells. *J. Am. Chem. Soc.* 130, 9638-9639 (2008).

34. A. R. Lippert, K. R. Keshari, J. Kurhanewicz, C. J. Chang, A hydrogen peroxide-responsive hyperpolarized $^{13}C$ MRI contrast agent. *J. Am. Chem. Soc.* 133, 3776-3779 (2011).
35. M. Abo, et al, Development of a highly sensitive fluorescence probe for hydrogen peroxide. *J. Am. Chem. Soc.* 133, 10629-10637 (2011).
36. Y. Hitomi, T. Takeyasu, T. Funabiki, M. Kodera, Detection of enzymatically generated hydrogen peroxide by metal-based fluorescent probe. *Anal. Chem.* 83, 9213-9216 (2011).
37. S. Ye, J. J. Hu, D. Yang, Tandem Payne/Dakin Reaction: A New Strategy for Hydrogen Peroxide Detection and Molecular Imaging. *Angew. Chem. Int. Ed.* 57, 10173-10177 (2018).
38. S. Ye, et al., A highly selective and sensitive chemiluminescent probe for realtime monitoring of hydrogen peroxide in cells and animals. *Angew. Chem. Int. Ed.* 59, 1-6 (2020).
39. K. J. Bruemmer, et al, Activity-based sensing: a synthetic methods approach for selective molecular imaging and beyond. *Angew. Chem. Int. Ed.* 59, 13734-13762 (2020).
40. D. Pham, U. Basu, I. Pohorilets, C. M. S. Croix, S. C. Watkins, K. Koide, Fluorogenic probe using a mislow-evans rearrangement for real-time imaging of hydrogen peroxide. *Angew. Chem. Int. Ed.* (2020).
41. V. V. Belousov et al., Genetically encoded fluorescent indicator for intracellular hydrogen peroxide. *Nature Methods* 3, 281-286 (2006).
42. K. N. Markvicheva et al., A genetically encoded sensor for $H_2O_2$ with expanded dynamic range. *Bioorg. Med Chem.* 19, 1079-1084 (2011).
43. D. S. Bilan et al., HyPer-3: a genetically encoded $H_2O_2$ probe with improved performance for ratiometric and fluorescence lifetime imaging. *ACS Chem. Biol.* 8, 535-542 (2013).
44. M. Gutscher et al., Proximity-based protein thiol oxidation by $H_2O_2$-scavenging peroxidases. *J. Biol. Chem.* 284, 31532-31540 (2009).
45. B. Morgan et al., Real-time monitoring of basal $H_2O_2$ levels with peroxiredoxin-based probes. *Nature Chem. Biol.* 12, 437-443 (2016).
46. T. Doura, et al. Detection of lacZ-positive cells in living tissue with single-cell resolution, *Angew. Chem. Int. Ed.,* 55, 9620-9624 (2016).
47. H. Ito, et al. Red-shifted fluorogenic substrate for detection of lacZ-positive cells in living tissue with single-cell resolution, *Angew. Chem. Int. Ed.,* 57, 15702-15706 (2018).
48. M. Chiba, et al. Activatable photosensitizer for targeted ablation of lacZ-positive cells with single-cell resolution, *ACS Cent. Sci.* 5, 1676-1681 (2019).
49. J. Zhang, Y-Q. et al., Fluorescent probe for biological signaling molecule $H_2S$ based on a specific $H_2S$ trap group. *Chem. Commum.,* 49, 11305-11307 (2013).
50. C. Y-S. Chung, G. A. Timblin, K. Saijo, C. J. Chang, Versatile histochemical approach to detection of hydrogen peroxide in cells and tissues based on puromycin staining. *J. Am. Chem. Soc.* 140, 6109-6121 (2018).
51. M. L. Block, L. Zecca, J-S. Hong, Microglia-mediated neurotoxicity: uncovering the molecular mechanisms. *Nat. Rev. Neurosci.* 8, 57-69 (2007).
52. M. A. Yenari, T. M. Kauppinen, R. A. Swanson, Microglial activation in stroke: therapeutic targets. *Neurotherapeutics* 7, 378-391 (2007).
53. S. Hickman, S. Izzy, P. Sen, L. Morsett, J. E. Khoury, Microglia in neurodegeneration. *Nat. Neurosci* 21, 1359-1369 (2018).
54. A. I. Faden, et al., Progressive inflammation-mediated neurodegeneration after traumatic brain or spinal cord injury. *Br. J. Pharmacol.* 173, 681-691 (2016).
55. L. Qin, Y. et al., NADPH oxidase mediates lipopolysaccharide-induced neurotoxicity and proinflammatory gene expression in activated microglia. *J. Biol. Chem.* 279, 1415-1421 (2004).
56. J. Ohata, L. Krishnamoorthy, M. A. Gonzalez, T. Xiao, D. A. Iovan, F. D. Toste, E. W. Miller, C. J. Chang, An activity-based methionine bioconjugation approach to developing proximity-activated imaging reporters. *ACS Cent. Sci.* 6, 32-40 (2020).
57. S. Lee, C. et al., Activity-based sensing with a metal-directed acyl imidazole strategy reveals cell type-dependent pools of labile brain copper. *J. Am. Chem. Soc.* (2020).

Supplementary Information

Reagents and Instruments.

General chemicals were purchased from Tokyo Chemical Industries, Aldrich Chemical Co., and ThermoFisher, and were used without purification unless otherwise noted. $^1H$ NMR, $^{13}C$ NMR, and $^{19}F$ NMR spectra were recorded using Bruker AVB-400, AVQ-400, and AV-300 spectrometers at the College of chemistry NMR Facility at the University of California, Berkeley. Low-resolution electrospray mass spectral analyses were performed using a LC-MS (Advion Expression-L Compact MS, ESI source). High-resolution mass spectra were measured at the College of chemistry Mass Spectrometry Facility at the University of California, Berkeley. Fluorescence spectra were measured using a Photon Technology International Quanta Master 4 L-format scan spectrofluorometer equipped with an LPS-220B 75-W xenon lamp and power supply, A-1010B lamp housing with integrated igniter, switchable 814 photocounting/analog photomultiplier detection unit, and MD5020 motor driver. Fluorescence images were obtained with a Zeiss LSM 880 confocal laser scanning microscopy system, excited at 488 nm using a 500-650 nm filter for PG1-FM. Cell viability assay on 96-well plates was performed with a synergy plate reader (BioTek).

Synthesis.

Compound 1.

Compound 1 was synthesized according to literature procedures.

Compound 2

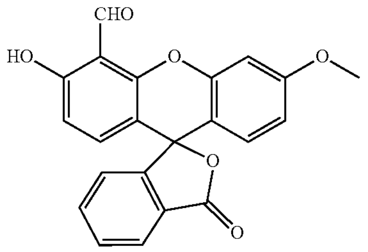 [SMILES: COc1ccc2c(c1)Oc1c(ccc(O)c1C=O)C21OC(=O)c2ccccc21]

To a stirred solution of compound 1 (2.4 g, 6.9 mmol) in trifluoroacetic acid (70 mL) was added hexamethylenetetramine (1.0 g, 7.6 mmol, 1.1 equiv). The mixture was stirred at 90° C. for 16 h and then $H_2O$ (70 mL) was added to the mixture. The resulting mixture was stirred at 95° C. for another 1 h, and then cooled to room temperature. The mixture was extracted with $CH_2Cl_2$ three times, dried over $Na_2SO_4$, and evaporated. The crude product was purified by silica-gel column chromatography (eluent: $CH_2Cl_2$/MeOH=100/0 to 100/1) to yield 900 mg (34%) of 2 as a white solid. $^1H$ NMR (300 MHz, $CDCl_3$) δ 12.17 (s, 1H), 10.68 (s, 1H), 8.10-7.97 (m, 1H), 7.67 (ddd, J=8.8, 7.2, 1.3 Hz, 2H), 7.21-7.12 (m, 1H), 6.91 (d, J=8.9 Hz, 1H), 6.86-6.80 (m, 1H), 6.80-6.49 (m, 3H), 3.89-3.80 (m, 4H); $^{13}C$ NMR (101 MHz, $CDCl_3$) δ 193.38, 169.20, 164.56, 161.65, 153.26, 152.66, 151.40, 137.15, 135.42, 130.20, 129.27, 126.80, 125.36, 123.93, 113.92, 112.78, 111.12, 109.81, 109.01, 101.05, 82.09, 55.81. LRMS: calcd for $[M+H]^+$, 375.0; found 375.0.

Compound 3

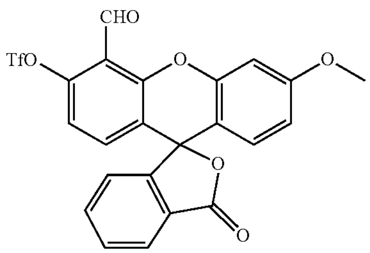 [SMILES: COc1ccc2c(c1)Oc1c(ccc(OS(=O)(=O)C(F)(F)F)c1C=O)C21OC(=O)c2ccccc21]

A mixture of compound 2 (900 mg, 2.4 mmol), N-phenyl-bis(trifluoromethanesulfonimide) (1.28 g, 3.6 mmol, 1.5 equiv) and $Cs_2CO_3$ (1.56 g, 4.8 mmol, 2.0 equiv) in MeCN (30 mL) was stirred at ambient temperature for 1 h. After the filtration, the filtrate was evaporated under the reduced pressure. The resulting residue was purified by silica-gel column chromatography with $CH_2Cl_2$ eluent to yield 1.2 g (98%) of 3 as a pale yellow solid. $^1H$ NMR (300 MHz, $CDCl_3$) δ 10.79 (d, J=0.7 Hz, 1H), 8.11-8.02 (m, 1H), 7.80-7.63 (m, 2H), 7.20 (dt, J=7.6, 0.9 Hz, 1H), 7.13 (d, J=8.8 Hz, 1H), 7.00 (d, J=8.8 Hz, 1H), 6.88 (dd, J=2.2, 0.7 Hz, 1H), 6.76-6.72 (m, 2H), 3.87 (s, 3H); $^{13}C$ NMR (101 MHz, $CDCl_3$) δ 185.57, 168.87, 162.08, 153.68, 152.27, 151.27, 148.34, 135.80, 134.87, 130.65, 129.73, 129.05, 127.52, 126.22, 125.70, 123.95, 123.64, 121.41, 117.78, 117.32, 113.54, 110.32, 101.19, 80.97, 77.48, 77.36, 77.16, 76.84, 55.93; $^{19}F$ NMR (376 MHz, $CDCl_3$) δ-72.38. LRMS: calcd for $[M]^+$, 506.0; found 506.9.

Compound 4

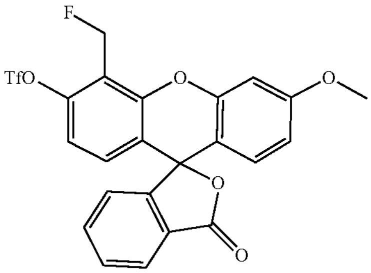 [SMILES: COc1ccc2c(c1)Oc1c(ccc(OS(=O)(=O)C(F)(F)F)c1CF)C21OC(=O)c2ccccc21]

To a solution of compound 3 (50 mg, 0.098 mmol) in THF-MeOH (2 mL/2 mL) was added AcOH (6 mL, 0.098 mmol, 1.0 equiv) and $NaBH(OAc)_3$ (25 mg, 0.118 mmol, 1.2 equiv). The mixture was stirred for 1 h at ambient temperature under $N_2$ atmosphere, diluted with sat. $NH_4Cl$ aq., and then extracted with EtOAc three times. The combined organic layer was dried over $Na_2SO_4$, and concentrated. The crude product was dissolved in $CH_2Cl_2$ (10 mL) and cooled to −20° C. (Dimethylamino)sulfur trifluoride (DAST, 15 mL, 0.118 mmol, 1.2 equiv) was added to the mixture in one portion and stirred at ambient temperature for 1 h. After addition of MeOH to quench excess of DAST, the mixture was evaporated. The crude product was purified by silica-gel column chromatography with $CH_2Cl_2$ eluent to yield 40 mg (80%) of 4 as a white solid. $^1H$ NMR (400 MHz, $CDCl_3$) δ 8.05 (dq, J=7.4, 0.9 Hz, 1H), 7.76-7.62 (m, 2H), 7.19 (dt, J=7.5, 0.9 Hz, 1H), 7.07 (d, J=8.9 Hz, 1H), 6.97 (ddd, J=8.9, 2.3, 0.7 Hz, 1H), 6.88 (d, J=2.4 Hz, 1H), 6.76-6.65 (m, 2H), 5.95-5.61 (m, 2H), 3.87 (d, J=0.7 Hz, 3H); $^{13}C$ NMR (101 MHz, $CDCl_3$) δ 169.00, 161.93, 152.58, 151.75, 151.26, 149.13, 135.61, 131.20, 130.43, 129.04, 126.40, 125.54, 124.03, 120.35, 117.21, 116.64, 113.14, 110.49, 101.13, 81.66, 73.90, 72.23, 55.87, 30.45, 29.84; 19F NMR (376 MHz, $CDCl_3$) δ-72.43, −210.36. LRMS: calcd for $[M+H]^+$, 511.0; found 511.0.

Compound 5 (Peroxy Green 1—Fluoromethyl, PG1-FM)

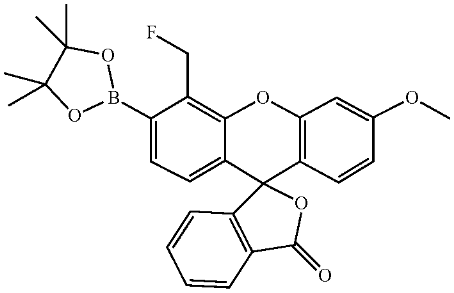

A mixture of 4 (160 mg, 0.31 mmol), bis(pinacolato) diboron (102 mg, 0.40 mmol, 1.3 equiv), $Pd(dppf)Cl_2$ (22 mg, 0.031 mmol, 0.1 equiv), and potassium acetate (91 mg, 0.93 mmol, 3.0 equiv) in dioxane (3 mL) was stirred at 90° C. for 3 h. After being cooled, the reaction mixture was diluted with $CH_2Cl_2$, filtered over Celite pad and concentrated. The crude product was purified by silica-gel column chromatography with $CH_2Cl_2$ eluent and washing with MeOH to yield 90 mg (59%) of PG1-FM (5) as a white solid. $^1H$ NMR (300 MHz, $CDCl_3$) δ 8.03 (dd, J=6.1, 2.1 Hz, 1H), 7.63 (ddd, J=6.8, 4.7, 1.4 Hz, 2H), 7.46 (d, J=7.9 Hz, 1H), 7.11 (dd, J=6.4, 2.1 Hz, 1H), 6.91-6.79 (m, 2H), 6.72 (d, J=8.8 Hz, 1H), 6.63 (dd, J=8.8, 2.5 Hz, 1H), 6.03 (d, $J_{H\text{-}F}$=47.1 Hz, 2H), 3.86 (s, 3H), 1.35 (d, J=1.3 Hz, 13H); $^{13}C$ NMR (101 MHz, $CDCl_3$) δ 169.57, 161.65, 153.55, 152.16, 149.98, 135.24, 130.19, 130.17, 129.94, 129.35, 129.20, 128.91, 128.48, 126.29, 125.28, 123.92, 121.74, 112.40, 110.82, 101.07, 84.42, 82.53, 78.62, 55.77, 24.91; $^{19}F$ NMR (376 MHz, $CDCl_3$) δ-204.00. HRMS: calcd for $[M+H]^+$, 489.1879; found, 489.1883 (+0.0004 mmu).

Compound 6

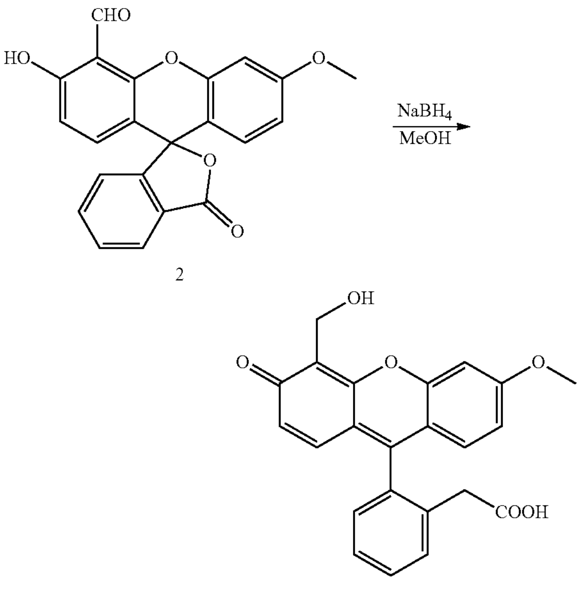

2

6

To a solution of compound 2 (40 mg, 0.106 mmol) in THF-MeOH (2 mL/2 mL) was added $NaBH_4$ (5 mg, 0.128 mmol, 1.2 equiv). The mixture was stirred for 16 h at ambient temperature under $N_2$ atmosphere, diluted with 2N HCl, and then extracted with EtOAc three times. The combined organic layer was dried over $Na_2SO_4$, and concentrated. The crude product was purified by silica-gel column chromatography (eluent: $CH_2Cl_2$/MeOH=100/2.5) and washing with MeOH to yield 20 mg (50%) of compound 6 as a yellow solid. $^1H$ NMR (300 MHz, $CDCl_3$) δ 8.04-7.95 (m, 1H), 7.72-7.54 (m, 2H), 7.21-7.09 (m, 1H), 6.72 (d, J=2.4 Hz, 1H), 6.69-6.51 (m, 4H), 5.28-5.14 (m, 2H), 3.79 (s, 3H). $^{13}C$ NMR (101 MHz, $CDCl_3$) δ 170.02, 161.54, 158.72, 152.80, 152.41, 149.11, 135.25, 129.91, 129.07, 128.24, 126.92, 125.23, 124.20, 113.29, 112.00, 111.75, 111.13, 110.50, 100.94, 58.24, 55.73. LRMS: calcd for $[M+H]^+$, 377.0; found 377.0.

Compound 7.

Compound 1 was synthesized according to literature procedures[2].

Compound 8

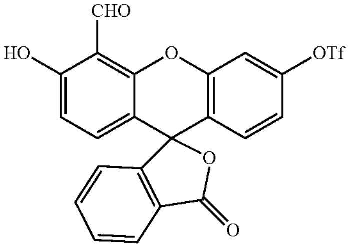 [SMILES: O=Cc1c(O)ccc2c1Oc1cc(OS(=O)(=O)C(F)(F)F)ccc1C21OC(=O)c2ccccc21]

To a stirred solution of compound 7 (3.0 g, 6.46 mmol) in trifluoroacetic acid (75 mL) was added hexamethylenetetramine (997 mg, 7.1 mmol, 1.1 equiv). The mixture was stirred at 90° C. for 16 h and then $H_2O$ (70 mL) was added to the mixture. The resulting mixture was stirred at 95° C. for another 1 h, and then cooled to room temperature. The mixture was extracted with $CH_2Cl_2$ three times, dried over $Na_2SO_4$, and evaporated. The crude product was purified by silica-gel column chromatography (eluent: $CH_2Cl_2$/MeOH=100/0 to 100/2.5) to yield 1.2 g (38%) of 8 as a pale yellow solid.

Compound 9

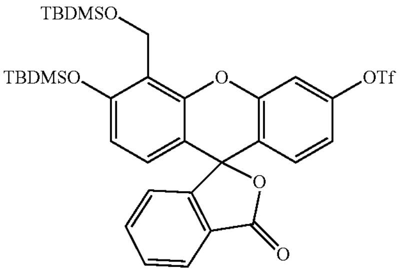 [SMILES: CC(C)(C)[Si](C)(C)OCc1c(O[Si](C)(C)C(C)(C)C)ccc2c1Oc1cc(OS(=O)(=O)C(F)(F)F)ccc1C21OC(=O)c2ccccc21]

To a solution of compound 8 (600 mg, 1.2 mmol) in THF-MeOH (24 mL/12 mL) and AcOH (72 μL) was added $NaBH(OAc)_3$ (600 mg, 2.83 mmol, 2.3 equiv). The mixture was stirred for 16 h at ambient temperature under $N_2$ atmosphere, diluted with Sat. $NH_4Cl$ aq. and then extracted with EtOAc three times. The combined organic layer was dried over $Na_2SO_4$, and concentrated. The crude product was purified by silica-gel column chromatography (eluent: $CH_2Cl_2$/MeOH=95/5) to yield 530 mg (89%) of hydroxymethyl compound as a pale yellow solid. A mixture of hydroxymethyl compound (900 mg, 2.4 mmol), TBDMS-Cl (970 mg, 6.4 mmol, 6.0 equiv), and Imidazole (583 mg, 8.56 mmol, 8.0 equiv) in DMF (5 mL) was stirred at 90° C. for 16 h. $H_2O$ was added to the reaction mixture and the mixture was extracted with AcOEt three times, dried over $Na_2SO_4$, and evaporated. The resulting residue was purified by silica-gel column chromatography with 100% $CH_2Cl_2$ eluent to yield 670 mg (80%) of 9 as a white solid.

Compound 10

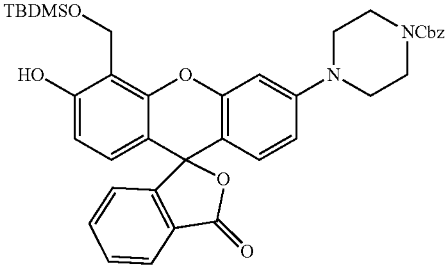 [SMILES: CC(C)(C)[Si](C)(C)OCc1c(O)ccc2c1Oc1cc(N3CCN(C(=O)OCc4ccccc4)CC3)ccc1C21OC(=O)c2ccccc21]

A mixture of compound 9 (480 mg, 0.66 mmol), 1-carbobenzoxypiperazine (307 μL, 3.6 mmol, 2.4 equiv), $Cs_2CO_3$ (432 mg, 1.32 mmol, 2.0 equiv), XantPhos, (115 mg, 0.19 mmol, 0.3 equiv) and $Pd_2(dba)_3$ (60 mg, 0.066 mmol, 0.1 equiv) in Dioxane (10 mL) was stirred at 80° C. for 3 h. After the filtration with celite, the filtrate was evaporated under the reduced pressure. To a solution of the obtained product in DMF (6 mL) was added 1N LiOH. The mixture was stirred at ambient temperature for 5 minutes, diluted with Sat. $NH_4Cl$ aq. and then extracted with EtOAc three times. The combined organic layer was dried over $Na_2SO_4$, and concentrated. The resulting residue was purified by silica-gel column chromatography with $CH_2Cl_2$/AcOEt=100/0 eluent to yield 670 mg (45%) of 10 as a red solid.

Compound 11

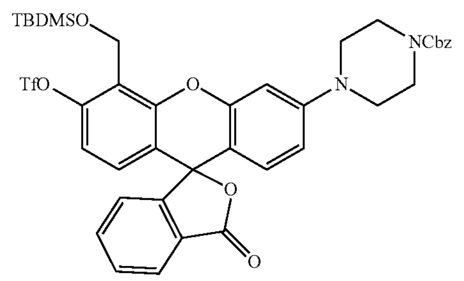 [SMILES: CC(C)(C)[Si](C)(C)OCc1c(OS(=O)(=O)C(F)(F)F)ccc2c1Oc1cc(N3CCN(C(=O)OCc4ccccc4)CC3)ccc1C21OC(=O)c2ccccc21]

A mixture of compound 10 (910 mg, 1.34 mmol), N-phenyl-bis(trifluoromethanesulfonimide) (655 mg, 2.0 mmol, 1.5 equiv) and $Cs_2CO_3$ (575 mg, 1.6 mmol, 1.2 equiv) in THE (50 mL) was stirred at ambient temperature for 1 h. After the filtration, the filtrate was evaporated under the reduced pressure. The resulting residue was purified by silica-gel column chromatography (eluent: $CH_2Cl_2$/AcOEt=100/0 to 95/5) to yield 550 mg (55%) of 11 as a pale yellow solid.

Compound 12

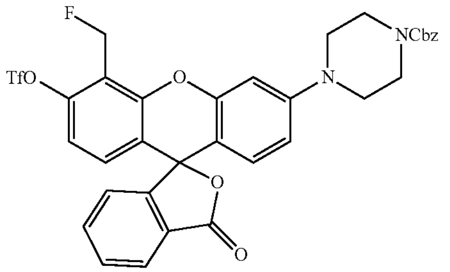 [SMILES: O=C1OC2(c3ccc(N4CCN(C(=O)OCc5ccccc5)CC4)cc3Oc3c2ccc(OS(=O)(=O)C(F)(F)F)c3CF)c2ccccc21]

To a solution of compound 11 (550 mg, 1.2 mmol) in THE (25 mL) was added hydrogen chloride solution 4.0 M in dioxane (2.75 mL). The mixture was stirred for 15 min at ambient temperature, diluted with Sat. $NaHCO_3$ aq. and then extracted with EtOAc three times. The combined organic layer was dried over $Na_2SO_4$, and concentrated. The crude product was dissolved in $CH_2Cl_2$ (60 mL) and cooled to −20° C. (Dimethylamino)sulfur trifluoride (DAST, 118 μL, 0.89 mmol, 1.2 equiv) was added to the mixture in one portion and stirred at ambient temperature for 2 h. After addition of MeOH to quench excess of DAST, the mixture was evaporated. The resulting residue was purified by silica-gel column chromatography with $CH_2Cl_2$/AcOEt=95/5 eluent to yield 340 mg (65%) of 12 as a pale yellow solid.

Compound 13

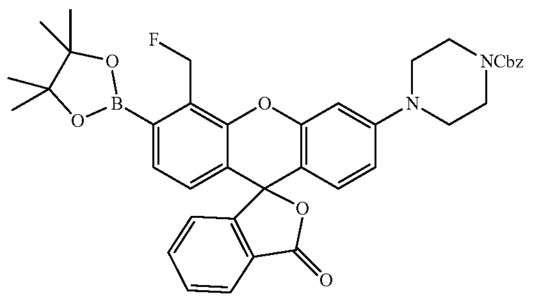 [SMILES: CC1(C)OB(c2ccc3c(c2CF)Oc2cc(N4CCN(C(=O)OCc5ccccc5)CC4)ccc2C32OC(=O)c3ccccc32)OC1(C)C]

A mixture of 12 (340 mg, 0.48 mmol), bis(pinacolato) diboron (160 mg, 0.63 mmol, 1.3 equiv), Pd(dppf)$Cl_2$ (35 mg, 0.048 mmol, 0.1 equiv), and potassium acetate (141 mg, 1.44 mmol, 3.0 equiv) in dioxane (3 mL) was stirred at 90° C. for 1.5 h. After being cooled, the reaction mixture was diluted with $CH_2Cl_2$, filtered over Celite pad and concentrated. The crude product was purified by silica-gel column chromatography with hexane/AcOEt=50/50 eluent and to yield 270 mg (83%) of 13 as a pale yellow solid.

Compound 14 (MitoPY1-FM)

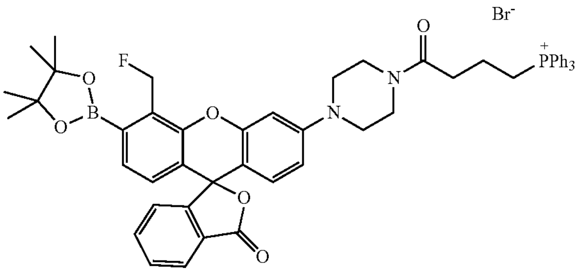

To a solution of compound 13 (100 mg, 1.47 mmol) in THF-EtOH (2 mL/2 mL) was added 10% Pd/C. The mixture was stirred for 15 min at ambient temperature under $H_2$ atmosphere. After the filtration, the filtrate was evaporated under the reduced pressure. A mixture of crude product (40 mg, 0.07 mmol), (3-carboxypropyl)triphenylphosphonium bromide (38 mg, 0.07 mmol, 1.0 equiv), and N,N-diisopropylethylamine (15 μL, 0.088 mmol, 2.0 equiv) in DMF (3 mL) was stirred at ambient temperature for 16 h. $H_2O$ was added to the reaction mixture and the mixture was extracted with AcOEt three times, dried over $Na_2SO_4$, and evaporated. The resulting residue was purified by washing with AcOEt twice to yield 30 mg (44%) of compound 14 (MitoPY1-FM) as a pale yellow solid.

Compound 15

Compound 15 was synthesized according to the literature[3].

Compound 16

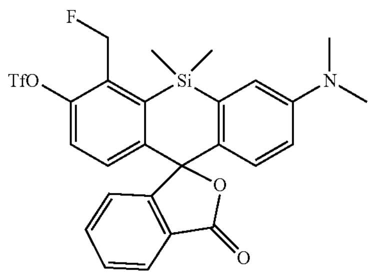 [SMILES: CN(C)c1ccc2c(c1)[Si](C)(C)c1c(ccc(OS(=O)(=O)C(F)(F)F)c1CF)C21OC(=O)c2ccccc21]

A mixture of compound 15 (70 mg, 0.12 mmol), N-phenyl-bis(trifluoromethanesulfonimide) (55 mg, 0.15 mmol, 1.2 eq) and $Cs_2CO_3$ (63 mg, 0.19 mmol, 1.5 eq) in THE (5 mL) was stirred at ambient temperature for 16 h. After the filtration, the filtrate was evaporated under the reduced pressure. To the resulting residue dissolved in THE (4 mL) was added 4N HCl in dioxane (1 mL), and then the reaction mixture was stirred at ambient temperature for 16 h. Sat. $NaHCO_3$ aq. was added to the reaction mixture, which was then extracted with EtOAc. The organic layer was dried over $Na_2SO_4$ and concentrated. The crude product was dissolved in $CH_2Cl_2$ (3 mL) and cooled to −20° C. DAST (23 ml, 0.17 mmol, 1.5 eq.) was added to the mixture in one portion and stirred at ambient temperature for 1 h. After addition of MeOH to quench excess of DAST, the mixture was evaporated. The crude product was purified by silica-gel column chromatography with $CH_2Cl_2$ eluent to yield 20 mg (29%) of compound 16 as a pale-yellow solid.

Compound 17 (PR1-FM)

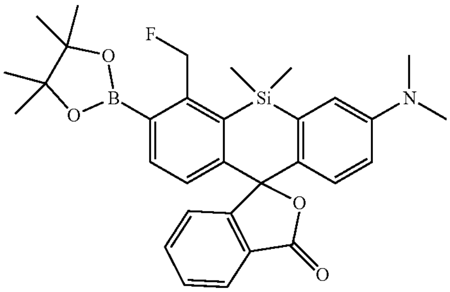

A mixture of compound 16 (20 mg, 0.035 mmol), bis (pinacolato)diboron (12 mg, 0.046 mmol, 1.3 eq), Pd(dppf) $Cl_2$ (3 mg, 0.0035 mmol, 0.1 eq.), and potassium acetate (10 mg, 0.105 mmol, 3.0 eq) in dioxane (1 mL) was stirred at 90° C. for 16 h. After being cooled, the reaction mixture was diluted with $CH_2Cl_2$, filtered over Celite pad and concentrated. The crude product was purified by silica-gel column chromatography (eluent: $CH_2Cl_2$/EtOAc=100/0 to 100/1) to yield 5 mg (26%) of compound 17 (PR1-FM) as a lime green solid.

ROS Selectivity Analysis.

PG1-FM was dissolved in DMSO to obtain a 1 mM stock solution. The fluorescence spectra of PG1-FM (1 μM) were measured in PBS (−) containing 25 μM of $H_2O_2$, $OCl^-$, TBHP, $O_2^-$, $ONOO^-$, or NO $OCl^-$, $O_2^-$, $ONOO^-$, or NO were generated by using NaOCl (Fluka), potassium superoxide (SIGMA), Peroxynitrite (Cayman), and PROLI NONOate (Cayman), respectively. The fluorescence spectra of PG1-FM were collected an emission window between 500 nm to 650 nm with excitation at 488 nm.

HPLC Analyses of the Reaction Between PG1-FM and $H_2O_2$.

PG1-FM (10 μM) and compound 5 (10 μM) were diluted with eluent (A/B=50/50(v/v)) or PBS (−) to prepare 100 μM solutions containing 1% DMSO. The reaction mixture of PG1-FM (100 μM) and $H_2O_2$ (10 μM) in PBS (−) was incubated at 37° C. for 30 min, and then analyzed by HPLC. LC analyses were performed on an Agilent Technologies 1200 system using eluent A ($H_2O$ containing 0.05% formic acid) and eluent B (acetonitrile containing 0.05% formic acid), and monitored at 254 nm and 470 nm.

SDS-PAGE Experiments in the Presence of BSA.

PG1-FM (10 μM) and BSA (0.5 mg/mL) were incubated at 25° C. for 1 h with or without $H_2O_2$ (100 μM). Afterward, Ebselen (100 μM) was added to the mixture to quench excess of $H_2O_2$. The obtained samples were separated with Novex™ Mini Gel (Thermo). The gel was first analyzed by ChemiDoc™ MP (Bio-Rad) to take a fluorescence images, and stained with Coomassie brilliant blue (CBB) Solution Cell Culture.

Cells were grown at the UC Berkeley Tissue Culture Facility. HeLa, RAW264.7, and A431 cells were cultured in DMEM (high glucose) supplemented with 10% (v/v) fetal bovine serum, GlutaMAX, and NEAA. All cells were maintained in a humidified 5% $CO_2$ incubator at 37° C.

Representative Live Cell Imaging Experiments: RAW264.7 Cells with Endogenous Stimulation.

RAW264.7 cells were plated on a μ-slide 8 well (ibidi) and cultured at 37° C. overnight in a 5% $CO_2$ incubator. The cells were pretreated with inhibitors, DPI (5 μM) or Ebselen (10 μM), for 30 min in HBSS. Afterward, the cells were co-incubated with PG1-FM (10 μM) and PMA (1 μg/mL) with or without DPI or Ebselen. The cells were observed on confocal microscope after washing with HBSS twice.

Flow Cytometric Analysis.

RAW264.7 cells were plated on a 6 well plate and cultured at 37° C. overnight in a 5% CO2 incubator. The cells were pretreated with inhibitors, DPI (5 μM) or Ebselen (10 μM), for 30 min in HBSS. Afterward, the cells were co-incubated with PG1-FM (5 μM) and PMA (1 μg/mL) with or without DPI or Ebselen. The cells were harvested by 0.05% Trypsin with EDTA, filtered, and analyzed with flow cytometer.

Supp References

Zhang J, Sun Y Q, Liu J, Shi Y, Guo W (2013) Fluorescent probe for biological signaling molecule $H_2S$ based on a specific $H_2S$ trap group. *Chem. Commum* 49:11305-11307.

B. C. Dickinson, C. Huynh, C. J. Chang (2010) A palette of fluorescent probes with varying emission colors for imaging hydrogen peroxide signaling in living cells. *JACS* 132:5906-5915.

H. Ito et al., Red-shifted fluorogenic substrate for detection of lacZ-positive cells in living tissue with single-cell resolution. *Angew. Chem. Int. Ed.* 57, 15702-15706 (2018).

Scheme 1. Synthesis of PG1-FM.

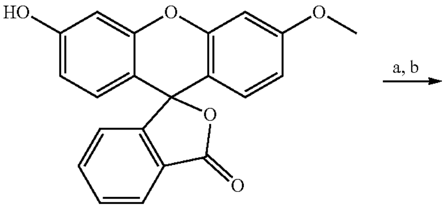

1

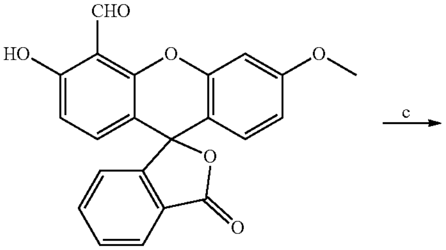

2

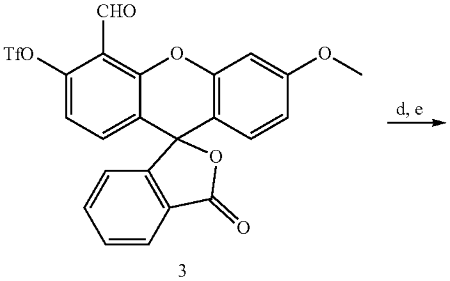

3

-continued
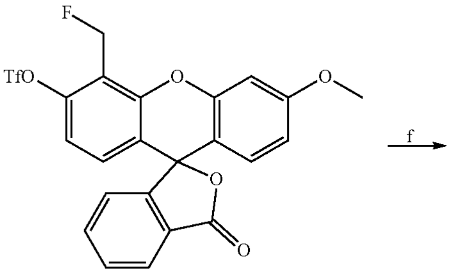
4
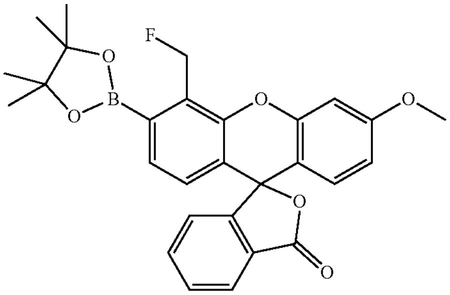
5
(PG1-FM)
Reagents and conditions: (a) hexamethylenetetramine, TFA, 90° C., 16 h; (b) $H_2O$, 95° C., 1 h; (c) N-phenyl-bis(trifluoromethanesulfonimide), $Cs_2CO_3$, MeCN, r.t., 1 h; (d) $NaBH(OAc)_3$, AcOH, THF/MeOH, 1 h; (e) DAST, $CH_2Cl_2$, -20° C. to r.t. 1 h; (f) Bis(pinacolato)diboron, $Pd(dppf)Cl_2$, KOAc, Dioxane, 80° C., 3 h.
Scheme 2. Synthetic route to MitoPY1-FM.
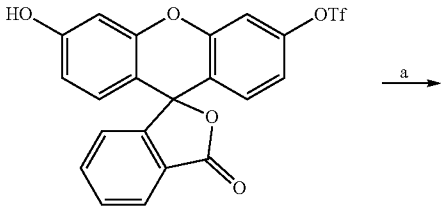
7
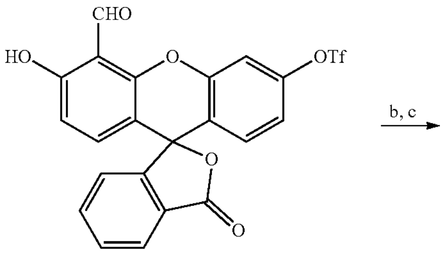
8
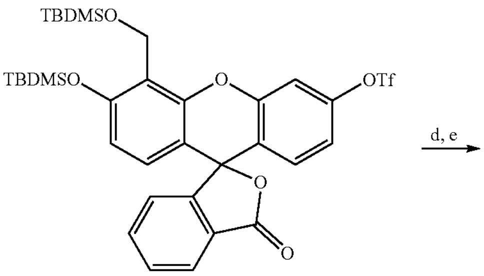
9
-continued
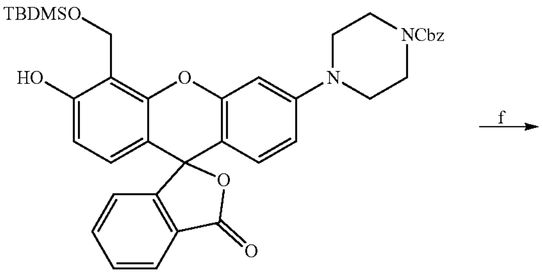
10
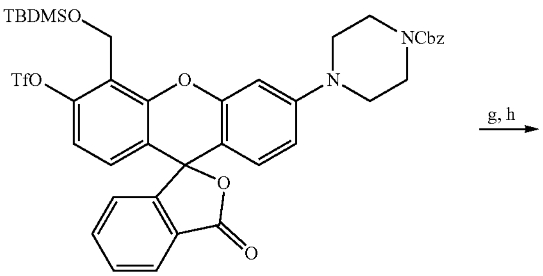
11
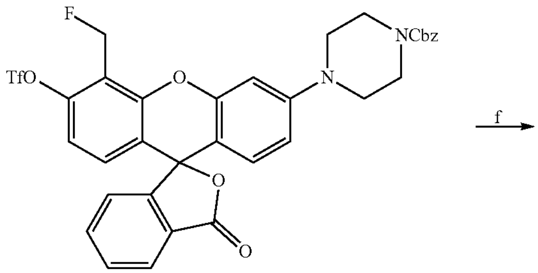
12
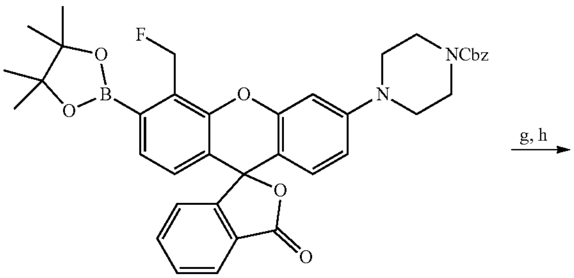
13

-continued

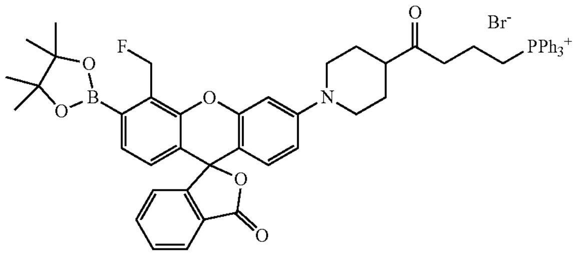

14
(MitoPY1-FM)

Reagents and conditions:
(a) hexamethylenetetramine, TFA, 90° C., 16 h;
(b) $H_2O$, 95° C., 1 h;
(c) $NaBH(OAc)_3$, AcOH, THF/MeOH, 1 h.;
(d) TBDMS-Cl, Imidazole, DMF, 90° C., 16 h;
(e) 1-carbobenzoxypiperazine, $Cs_2CO_3$, XantPhos, $Pd_2(dba)_3$, Dioxane, 80° C., 3 h;
(f) 1N LiOH, DMF, r.t., 5 min;
(g) $Ph(Tf)_2$, $Cs_2Co_3$, THF, r.t., 1 h; (h) 4N HCl-dioxane/THF, r.t., 15 min;
(i) DAST, $CH_2Cl_2$, -20° C. to r.t. 1 h;
(j) Bis(pinacolato)diboron, $Pd(dppf)Cl_2$, KOAc, Dioxane, 90° C., 16 h;
(k) Pd/C, $H_2$, THF-EtOH; (l) (3-carboxypropyl)triphenylphosphonium bromide, DIPEA, DMF, r.t., 16 h.

Scheme 3. Synthetic route to PR1-FM.

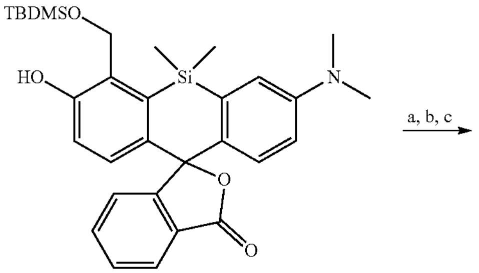

15

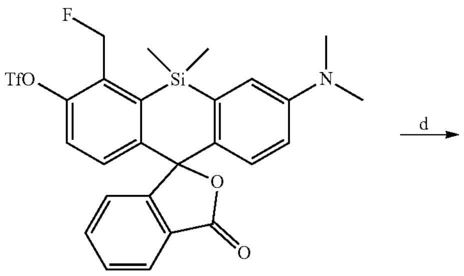

16

-continued

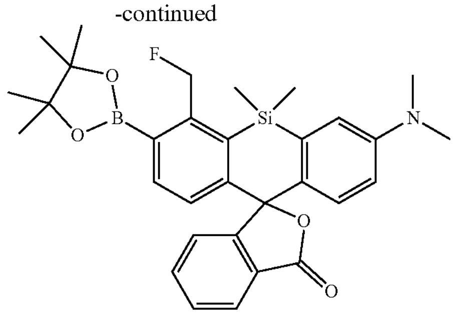

17
(PR1-FM)

Reagents and conditions:
(a) N-phenyl-bis(trifluoromethanesulfonimide), $Cs_2CO_3$, THF, r.t., 1 h;
(b) 4N HCl-dioxane/THF, r.t., 16 h;
(c) DAST, $CH_2Cl_2$, -20° C. to r.t. 1 h;
(d) Bis(pinacolato)diboron, $Pd(dppf)Cl_2$, KOAc, Dioxane, 90° C., 16 h.

The invention claimed is:

1. A reactive oxygen species (ROS) sensor compound comprising-having a structure:

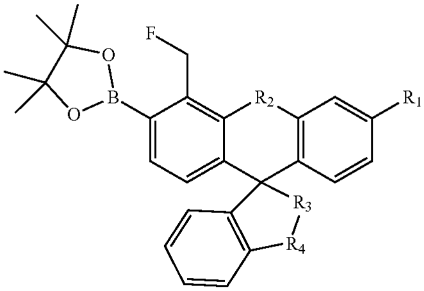

wherein:

R1 is OR5 or NR6R7, wherein R5, R6 and R7 are independently H, C1-C18 optionally substituted, optionally hetero-hydrocarbyl, or optionally substituted heteroatom, and R6/R7 are optionally joined to form a ring;

R2 is O, S, Se or Te, or an oxidized chalcogen selected from SO, $SO_2$, SS, SOS, SSS, SeO, $SeO_2$, SeS, SeOS, SeSS, TeO, $TeO_2$, TeS, TeOS, and TeSS; or CR8R9, SiR8R9, GeR8R9, or PR8R9; or NR10, BR10, or PR10; wherein R8-R10 are independently H, C1-C18 optionally substituted, optionally hetero-hydrocarbyl, or optionally substituted heteroatom;

R3 is O, S, Se, Te, or NR11, wherein R11 is H, C1-C18 optionally substituted, optionally hetero-hydrocarbyl, or optionally substituted heteroatom; and R4 is C, Si, C═O, or C═NR12, wherein R12 is H, C1-C18 optionally substituted, optionally hetero-hydrocarbyl, or optionally substituted heteroatom;

or a salt, hydrate or stereoisomer of the sensor compound.

2. The compound of claim 1, wherein:

R1 is OR5 or NR6R7, wherein R5, R6 and R7 are independently H or C1-C18 optionally substituted, optionally hetero-alkyl, and R6/R7 are optionally joined to form a ring.

3. The compound of claim 1, wherein:

R2 is O, S, Se or Te, or an oxidized chalcogen selected from SO, $SO_2$, SS, SOS, SSS, SeO, $SeO_2$, SeS, SeOS, SeSS, TeO, $TeO_2$, TeS, TeOS, and TeSS; or CR8R9, SiR8R9, GeR8R9, or PR8R9; or NR10, BR10, or PR10; wherein R8-R10 are independently H or C1-C18 optionally substituted, optionally hetero-alkyl.

4. The compound of claim 1, wherein:

R3 is O, S, Se, Te, or NR11, wherein R11 is H, C1-C18 optionally substituted, optionally hetero-alkyl.

5. The compound of claim 1, wherein:

R4 is C, Si, C═O, or C═NR12, wherein R12 is H, C1-C18 optionally substituted, optionally hetero-alkyl.

6. The compound of claim 1, wherein:

R1 is OR5 or NR6R7, wherein R5, R6 and R7 are independently H or C1-C18 optionally substituted, optionally hetero-alkyl, and R6/R7 are optionally joined to form a ring;

R2 is O, S, Se or Te, or an oxidized chalcogen selected from SO, $SO_2$, SS, SOS, SSS, SeO, $SeO_2$, SeS, SeOS, SeSS, TeO, $TeO_2$, TeS, TeOS, and TeSS; or CR8R9, SiR8R9, GeR8R9, or PR8R9; or NR10, BR10, or PR10; wherein R8-R10 are independently H or C1-C18 optionally substituted, optionally hetero-alkyl;

R3 is O, S, Se, Te, or NR11, wherein R11 is H, C1-C18 optionally substituted, optionally hetero-alkyl; and R4 is C, Si, C═O, or C═NR12, wherein R12 is H, C1-C18 optionally substituted, optionally hetero-alkyl.

7. The compound of claim 1, wherein:

R1 is OMe or NR6R7, wherein R6 and R7 are independently C1-C4 optionally substituted, optionally hetero-alkyl, and R6/R7 are optionally joined to form a ring.

8. The compound of claim 1, wherein:

R2 is O or $Si(CH_3)_2$.

9. The compound of claim 1, wherein:

R3 is O.

10. The compound of claim 1, wherein:

R4 is C═O.

11. The compound of claim 1, wherein:

R1 is OMe or NR6R7, wherein R6 and R7 are independently C1-C4 optionally substituted, optionally hetero-alkyl, and R6/R7 are optionally joined to form a ring;

R2 is O or $Si(CH_3)_2$;

R3 is O; and

R4 is C═O.

12. The compound of claim 1, having a structure:

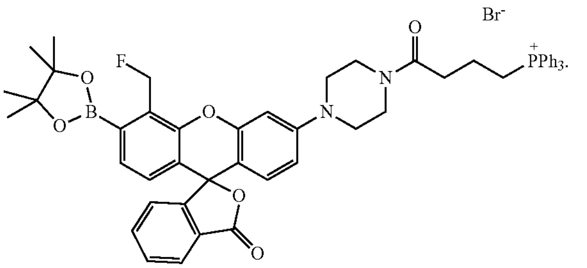

(MitoPY1-FM)

13. The compound of claim 1, having a structure:

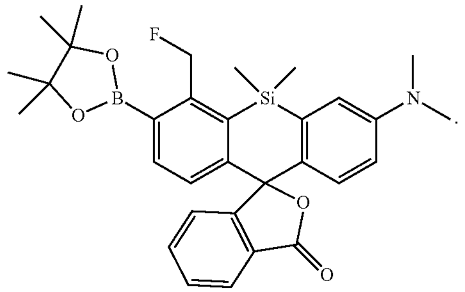

(PR1-FM)

14. The compound of claim 1, having a structure:

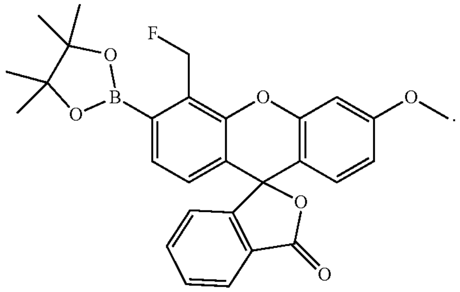

PG1-FM

15. The compound of claim 1, which is a bromide ($Br^-$) salt of the compound.

16. A method of using the compound of claim 1, comprising the step of reacting the compound with a ROS, thereby selectively detecting the ROS.

17. The method of claim 16, wherein the ROS is selected from hydrogen peroxide ($H_2O_2$), peroxynitrite, and organic peroxides.

18. The method of claim 16, wherein the reacting step provides boronate oxidation sensing or quinone methide labeling upon reaction with the ROS.

19. The method of claim 16, wherein the reacting step provides tandem boronate oxidation sensing and quinone methide labeling upon reaction with the ROS.

20. The method of claim 16, wherein the reacting step provides tandem boronate oxidation sensing and quinone methide labeling upon reaction with the ROS, to covalently trap the sensor compound in a cell and thereby provide a stain that preserves spatial information on localized ROS fluxes.

* * * * *